United States Patent
Yogo et al.

(10) Patent No.: US 10,203,257 B2
(45) Date of Patent: Feb. 12, 2019

(54) PHYSICAL-QUANTITY DETECTION DEVICE

(71) Applicant: HITACHI AUTOMOTIVE SYSTEMS, LTD., Ibaraki (JP)

(72) Inventors: Takayuki Yogo, Ibaraki (JP); Hiroaki Hoshika, Ibaraki (JP); Takahiro Miki, Ibaraki (JP)

(73) Assignee: HITACHI AUTOMOTIVE SYSTEMS, LTD., Ibaraki (JP)

( * ) Notice: Subject to any disclaimer, the term of this patent is extended or adjusted under 35 U.S.C. 154(b) by 233 days.

(21) Appl. No.: 15/326,975

(22) PCT Filed: Jun. 15, 2015

(86) PCT No.: PCT/JP2015/067114
§ 371 (c)(1),
(2) Date: Jan. 17, 2017

(87) PCT Pub. No.: WO2016/017301
PCT Pub. Date: Feb. 4, 2016

(65) Prior Publication Data
US 2017/0205261 A1 Jul. 20, 2017

(30) Foreign Application Priority Data
Jul. 30, 2014 (JP) .................... 2014-155049

(51) Int. Cl.
*G01F 1/50* (2006.01)
*G01K 1/08* (2006.01)
(Continued)

(52) U.S. Cl.
CPC .......... *G01L 19/0092* (2013.01); *F02D 41/18* (2013.01); *G01F 1/50* (2013.01);
(Continued)

(58) Field of Classification Search
CPC ....... G01F 1/50; G01L 19/0092; G01L 23/24; G01L 2019/0053
See application file for complete search history.

(56) References Cited

U.S. PATENT DOCUMENTS

| 5,469,749 A | 11/1995 | Shimada et al. |
| 2006/0037404 A1 | 2/2006 | Watanabe |

(Continued)

FOREIGN PATENT DOCUMENTS

| EP | 2154494 A1 | 2/2010 |
| JP | 59-20150 U | 2/1984 |

(Continued)

OTHER PUBLICATIONS

Extended European Search Report dated Feb. 27, 2018 for the European Patent Application No. 15827481.1.

*Primary Examiner* — Paul M. West
(74) *Attorney, Agent, or Firm* — Volpe and Koenig, P.C.

(57) ABSTRACT

In order to improve sensor characteristics and minimize variation in said characteristics, a pressure sensor is positioned upstream of a humidity sensor so as to help prevent water from contacting the humidity sensor and dust from adhering to the humidity sensor. This physical-quantity detection device 300 is characterized by having a detection unit 422 that detects humidity, a detection unit 421 that detects pressure, a circuit board 400 that has an electronic circuit that processes detection signals, and a housing 302 that accommodates the circuit board 400. The physical-quantity detection device 300 is also characterized in that the detection units 422, 421 are laid out on the surface of the circuit board 400 in a straight line in the direction in which a gas being measured flows, with the detection unit 421 that detects pressure positioned upstream of the detection unit 422 that detects humidity.

5 Claims, 21 Drawing Sheets

(51) Int. Cl.
    *F02D 41/18*      (2006.01)
    *F02M 35/10*      (2006.01)
    *G01F 1/684*      (2006.01)
    *G01L 19/00*      (2006.01)
    *G01L 23/24*      (2006.01)
    *G01N 19/10*      (2006.01)

(52) U.S. Cl.
    CPC ............... *G01F 1/684* (2013.01); *G01K 1/08* (2013.01); *G01L 23/24* (2013.01); *G01N 19/10* (2013.01); *F02D 2200/0406* (2013.01); *F02D 2200/0418* (2013.01); *F02M 35/10386* (2013.01); *F02M 35/10393* (2013.01)

(56)  References Cited

U.S. PATENT DOCUMENTS

| | | |
|---|---|---|
| 2008/0163683 A1 | 7/2008 | Becke et al. |
| 2008/0314118 A1 | 12/2008 | Bey, Jr. et al. |
| 2010/0031737 A1 | 2/2010 | Saito et al. |
| 2012/0085324 A1* | 4/2012 | Saito ............... F02M 35/10393 123/494 |
| 2013/0269419 A1 | 10/2013 | Etherington et al. |
| 2014/0116122 A1 | 5/2014 | Lammel et al. |

FOREIGN PATENT DOCUMENTS

| | | |
|---|---|---|
| JP | 2006-058137 A | 3/2006 |
| JP | 2006-170803 A | 6/2006 |
| JP | 2010-043883 A | 2/2010 |
| JP | 2010-151795 A | 7/2010 |

\* cited by examiner

PHYSICAL-QUANTITY DETECTION DEVICE

TECHNICAL FIELD

The present invention relates to a device that detects a physical-quantity of intake air of an internal combustion engine.

BACKGROUND ART

PTL 1 discloses a structure of a thermal type air flow rate sensor which includes a flow rate sensor element that measures an air flow rate, and an environmental sensor element that measures a physical quantity, and in which the flow rate sensor element is disposed in a sub-passage, the environmental sensor is disposed in a measurement chamber that is isolated from the sub-passage, and the environmental sensor is disposed on a main air-flow central side in comparison to the flow rate sensor element. In PTL 1, as the environmental sensor element, a humidity sensor element, a pressure sensor element, and a temperature sensor element are integrally formed on a common semiconductor substrate.

CITATION LIST

Patent Literature

PTL 1: Japanese Unexamined Patent Application Publication No. 2010-151795

SUMMARY OF INVENTION

Technical Problem

As disclosed in PTL 1, in a case of the structure in which the humidity sensor element and the pressure sensor element are integrally formed on the semiconductor substrate, there is a possibility that a water droplet or dust inflows in a state of being mixed in an air flow and adheres to each of the elements. Particularly, when a water droplet adheres to the humidity sensor element, there is a concern that accurate measurement may be obstructed until the water droplet is dried. In addition, when dust adheres to the humidity sensor element, there is a concern that characteristics may vary. It is necessary to provide a structure in which a water droplet and dust are less likely to reach the humidity sensor element so as to improve detection accuracy of the humidity sensor element and to reduce a variation in characteristics due to dust.

The invention has been made in consideration of the above-described situations, and an object thereof is to provide a physical-quantity detection device capable of reducing pour water and dust adherence to a humidity sensor element.

Solution to Problem

To solve the problem, according to an aspect of the invention, there is provided a physical-quantity detection device in which a humidity sensor element and a pressure sensor element are provided on the same circuit substrate, the humidity sensor element and the pressure sensor element are disposed on a flow line of the same passage, and at least one of the pressure sensor element is disposed upstream of the humidity sensor element.

Advantageous Effects of Invention

According to the aspect of the invention, it is possible to reduce pour water and dust adherence to the humidity sensor element with a simple structure. Furthermore, other objects, advantages, and features of the invention will be apparent from the following description of embodiments.

DESCRIPTION OF EMBODIMENTS

Figure 1:
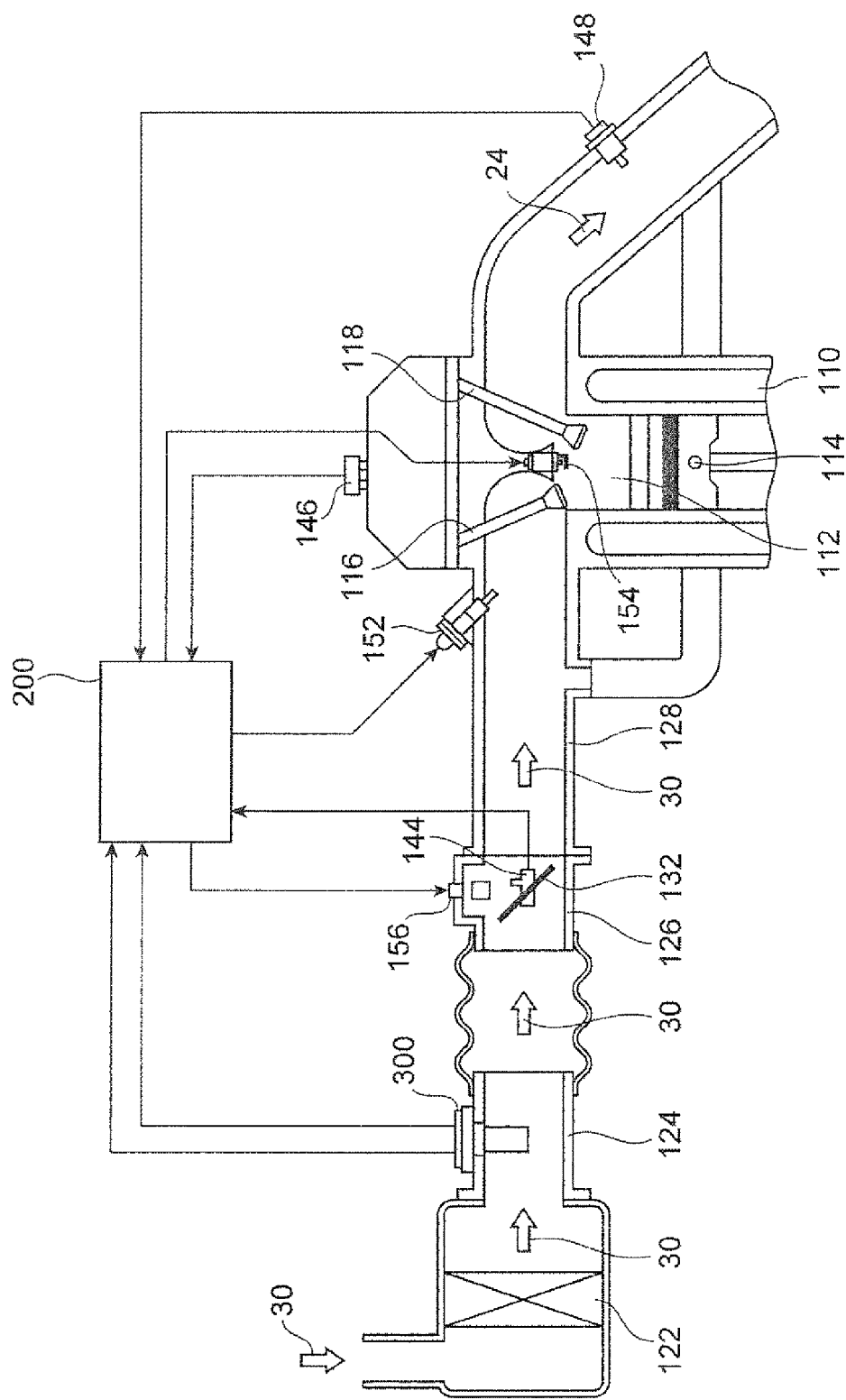
FIG. 1 is a system view illustrating one example in which a physical-quantity detection device according to the invention is used in an internal combustion engine control system.

The following aspects (hereinafter, referred to as examples) for carrying out the invention solve various problems which are demanded to be solved in actual products, solve various problems which are demanded to be preferably solved for use as a detection device that detects a physical quantity of intake air of, particularly, a vehicle, and can obtain various effects. One of the various problems which are solved by the following examples is the content described in the column of technical problem, and one of various effects exhibited by the following examples is the effect described in the column of advantages effects of the invention. The various problems solved by the following examples, and the various effects exhibited by the following examples will be described in description of the following examples. Accordingly, in description of the following examples, the problems solved by the examples or effects thereof also include contents other than the contents in the column of technical problem or the column of advantageous effects of the invention.

In the following examples, the same reference numeral represents the same configuration even though drawing numbers are different from each other, and attains the same operational effect. With respect to a configuration that is described already, only a reference numeral will be given, and description thereof may be omitted.

1. One Example in Which Physical-Quantity Detection Device According to Present Invention is Used in Internal Combustion Engine Control System FIG. 1 is a system view illustrating one example in which a physical-quantity detection device according to the invention is used in an electronic-fuel-injection-type internal combustion engine control system. On the basis of an operation of an internal combustion engine 110 including an engine cylinder 112 and an engine piston 114, intake air is suctioned from an air cleaner 122 as a gas to be measured 30, and is guided into a combustion chamber of the engine cylinder 112 through a main passage 124, for example, an intake body, a throttle body 126, and an intake manifold 128. A physical quantity of the gas to be measured 30, which is intake air that is guided to the combustion chamber, is detected by a physical-quantity detection device 300 according to the invention, and fuel is supplied from a fuel injection valve 152 on the basis of the physical quantity that is detected, and is guided to the combustion chamber in a mixed air state in combination with the intake air. Furthermore, in this example, the fuel injection valve 152 is provided in an intake port of the internal combustion engine. Fuel that is injected to the intake port forms a mixed gas in combination with the gas to be measured 30 that is intake air, and is guided to the combustion chamber through an intake valve 116. The mixed gas is combusted in the combustion chamber to generate mechanical energy.

The fuel and the air, which are guided to the combustion chamber, enter a state in which the fuel and the air are mixed with each other. The fuel and the air are explosively combusted by spark ignition of an ignition plug 154 to generate mechanical energy. The gas after being combusted is guided from an exhaust valve 118 to an exhaust pipe, and is discharged from the exhaust pipe to an outer side of a vehicle as an exhaust gas 24. A flow rate of the gas to be measured 30, which is intake air that is guided to the combustion chamber, is controlled by a throttle valve 132 of which an opening degree varies on the basis of an operation of an accelerator pedal. A fuel supply amount is controlled on the basis of the flow rate of the intake air that is guided to the combustion chamber, and a driver controls the opening degree of the throttle valve 132 to control the flow rate of the intake air that is guided to the combustion chamber. According to this, the driver can control mechanical energy that is generated by the internal combustion engine.

1.1 Overview of Control of Internal Combustion Engine Control System

A physical quantity such as a flow rate, a temperature, humidity, and a pressure of the gas to be measured 30, which is intake air that is taken-in from the air cleaner 122 and flows through the main passage 124, is detected by the physical-quantity detection device 300, and an electric signal indicating the physical quantity of the intake air is input to a control device 200 from the physical-quantity detection device 300. In addition, an output of a throttle angle sensor 144, which measures the opening degree of the throttle valve 132, is input to the control device 200. In addition, positions and states of the engine piston 114, the intake valve 116, and the exhaust valve 118 of the internal combustion engine, and an output of a rotation angle sensor 146 for measurement of a rotational speed of the internal combustion engine are input to the control device 200. An output of an oxygen sensor 148 is input to the control device 200 so as to measure a state of a mixed ratio between the amount of fuel and the amount of air from the state of the exhaust gas 24.

The control device 200 calculates a fuel injection amount and ignition time on the basis of the physical quantity of the intake air, which is an output of the physical-quantity detection device 300, and a rotational speed of the internal combustion engine which is measured on the basis of the output of the rotation angle sensor 146. The amount of fuel supplied from the fuel injection valve 152, and the ignition time by the ignition plug 154 are controlled on the basis of the calculation result. Actually, the fuel supply amount or the ignition time is further finely controlled on the basis of a temperature detected by the physical-quantity detection device 300, a variation state of a throttle angle, a variation state of an engine rotational speed, and a state of air-fuel ratio measured by the oxygen sensor 148. Furthermore, the control device 200 controls the amount of air that bypasses the throttle valve 132 in an idle driving state of the internal combustion engine by using an idle air control valve 156 to control a rotational speed of the internal combustion engine in the idle driving state.

1.2 Importance of Improvement in Detection Accuracy of Physical-Quantity Detection Device, and Mounting Environment of Physical-Quantity Detection Device A fuel supply amount and ignition time which are important control quantity of the internal combustion engine are calculated by setting the output of the physical-quantity detection device 300 as a main parameter. Accordingly, in the physical-quantity detection device 300, an improvement in the detection accuracy and suppression of a variation with the passage of time, and an improvement in reliability are important to secure an improvement in control accuracy and securement of reliability of a vehicle.

Particularly, a demand for fuel saving in a vehicle is high, and a demand for purification of an exhaust gas is very high. To cope with the demands, it is very important to improve detection accuracy for a physical quantity of intake air which is detected by the physical-quantity detection device 300. In addition, it is important for the physical-quantity detection device 300 to maintain high reliability.

A vehicle, on which the physical-quantity detection device 300 is mounted, is used in an environment in which a variation in a temperature or humidity is great. It is preferable for the physical-quantity detection device 300 to consider a countermeasure for a variation in a temperature or humidity, a countermeasure for dust, a contaminant, and the like in the use environment.

In addition, the physical-quantity detection device 300 is mounted in an intake pipe that is affected by heat generation from the internal combustion engine. Accordingly, the heat generation from the internal combustion engine is transferred to the physical-quantity detection device 300 through an intake pipe that is the main passage 124. The physical-quantity detection device 300 performs heat transfer with the gas to be measured 30 to detect the flow rate of the gas to be measured 30, and thus it is important to suppress an effect of heat from an outer side as much as possible.

The physical-quantity detection device 300 that is mounted on a vehicle solves the problem described in the column of technical problem, and can attain the effect described in the column of advantageous effects of the invention as to be described later. In addition, the physical-quantity detection device 300 solves various problems which are demanded to be solved in a product inconsideration of the above-described various problems, and attain various effect as to be described later. Specific problems to be solved by the physical-quantity detection device 300, or specific effects attained by the physical-quantity detection device 300 will be described in description of the following examples.

2. Configuration of Physical-Quantity Detection Device 300

2.1 External Structure of Physical-Quantity Detection Device 300

Figure 2:
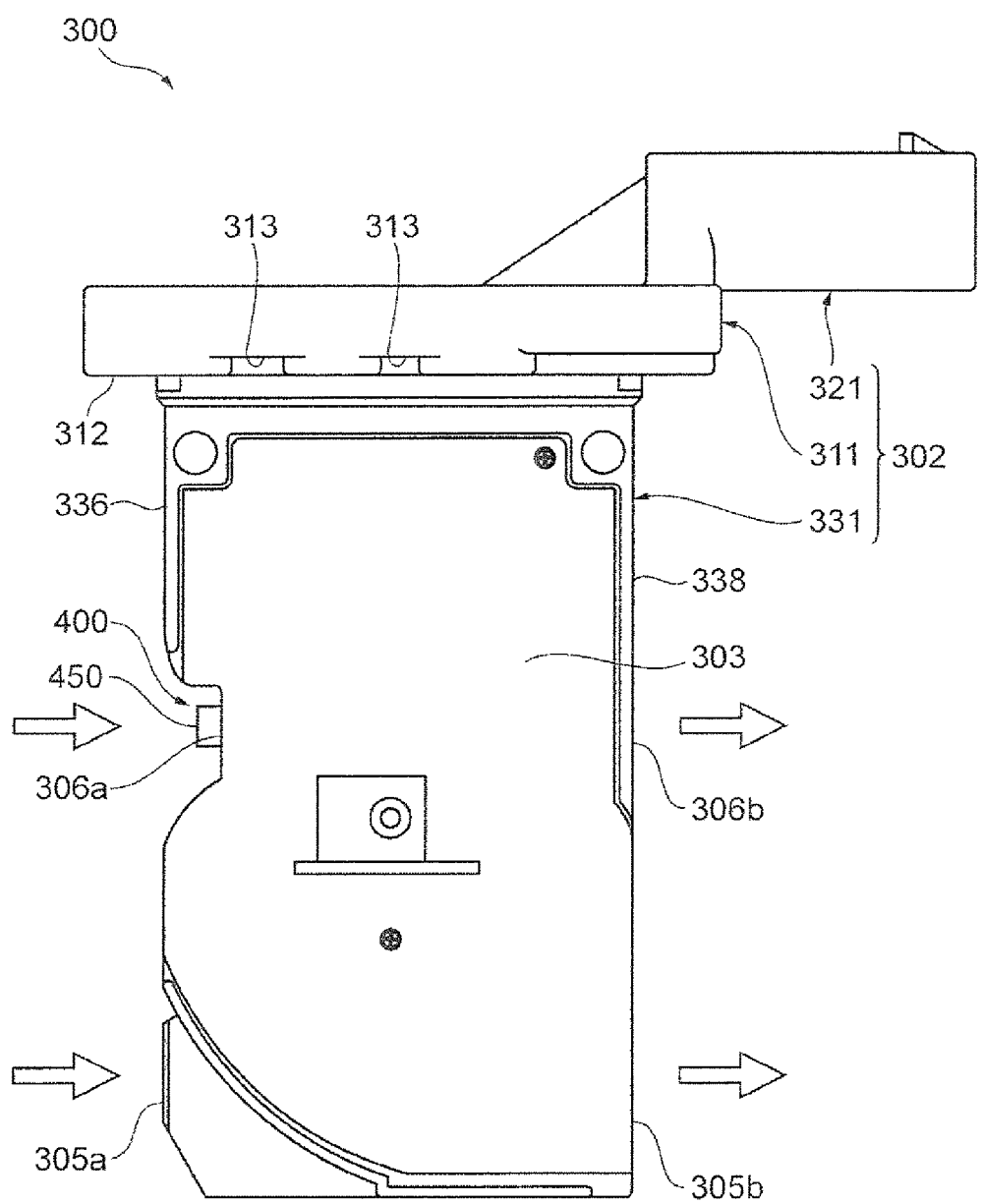
FIG. 2 is a front view of the physical-quantity detection device.
Figure 3:
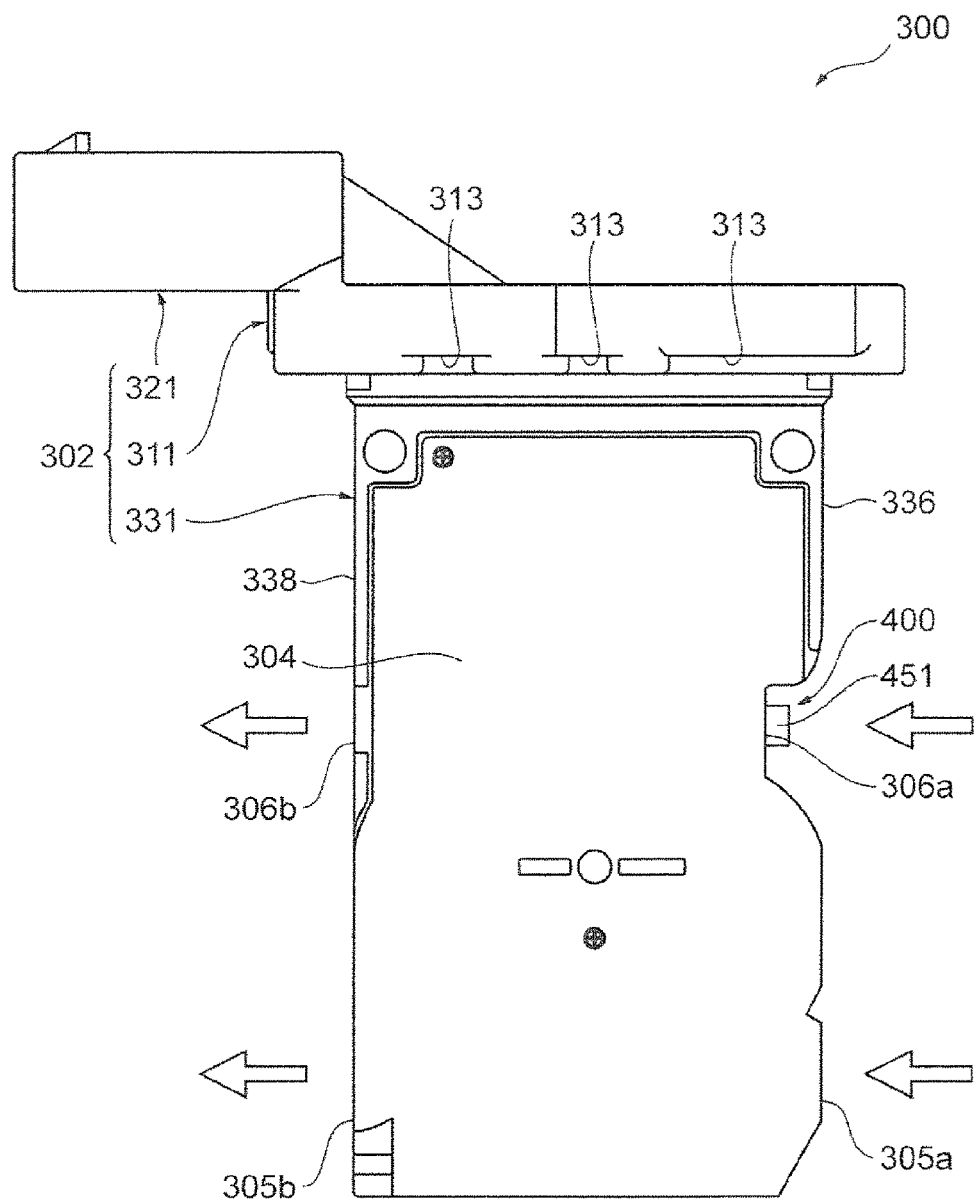
FIG. 3 is a rear view of the physical-quantity detection device.
Figure 4:
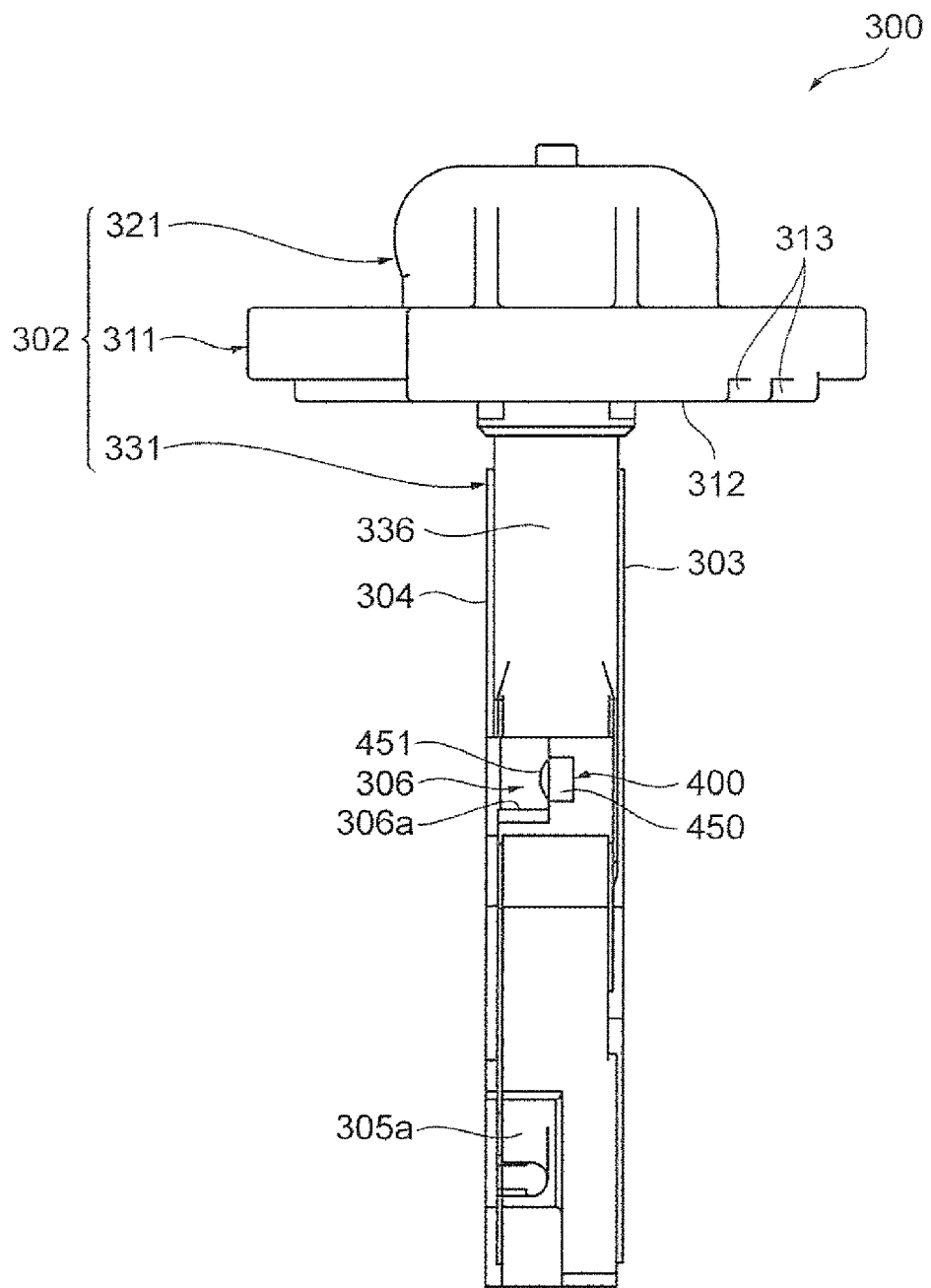
FIG. 4 is a left side view of the physical-quantity detection device.
Figure 5:
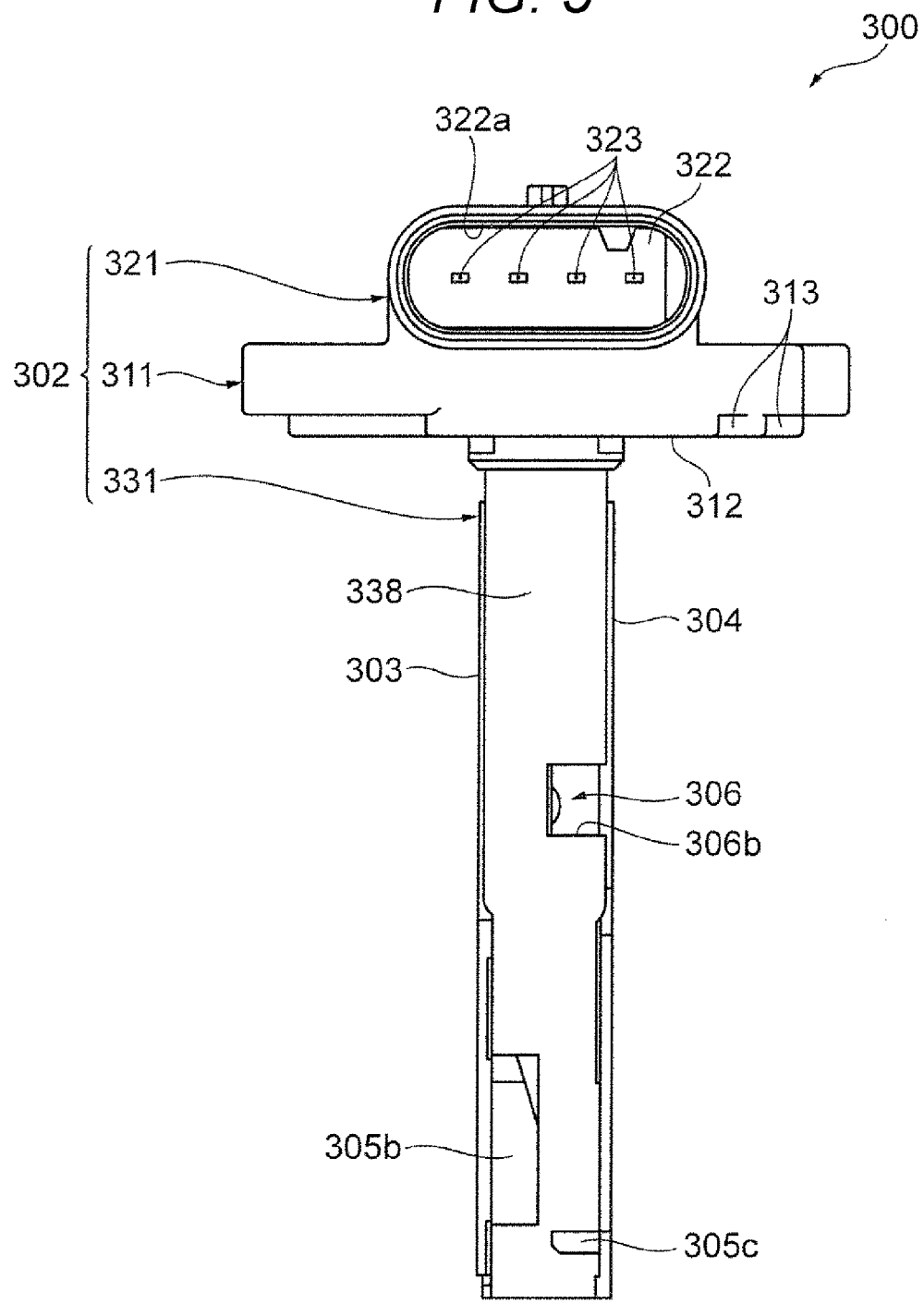
FIG. 5 is a right side view of the physical-quantity detection device.
Figure 6:
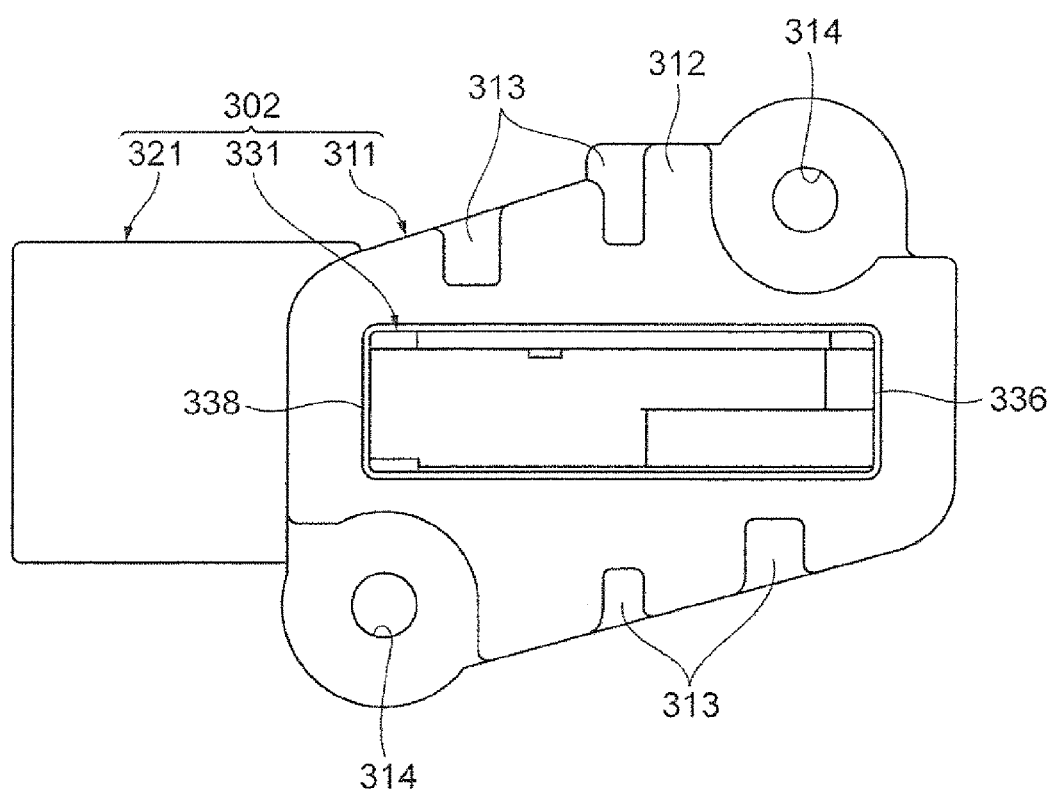
FIG. 6 is a bottom view of the physical-quantity detection device.

FIG. 2 to FIG. 6 are views illustrating an external appearance of the physical-quantity detection device 300. In the drawings, FIG. 2 is a front view of the physical-quantity detection device 300, FIG. 3 is a rear view thereof, FIG. 4 is a left side view thereof, FIG. 5 is a right side view thereof, and FIG. 6 is a bottom view thereof.

The physical-quantity detection device 300 includes a housing 302, a front cover 303, and a rear cover 304. The housing 302 is configured by molding a synthetic resin material, and includes a flange 311 that fixes the physical-quantity detection device 300 to the intake body that is the main passage 124, an external connection section 321 that protrudes from the flange 311 and includes a connector for establishment of electrical connection with an external device, and a measurement section 331 that extends to protrude toward the center of the main passage 124 from the flange 311.

Figure 7:
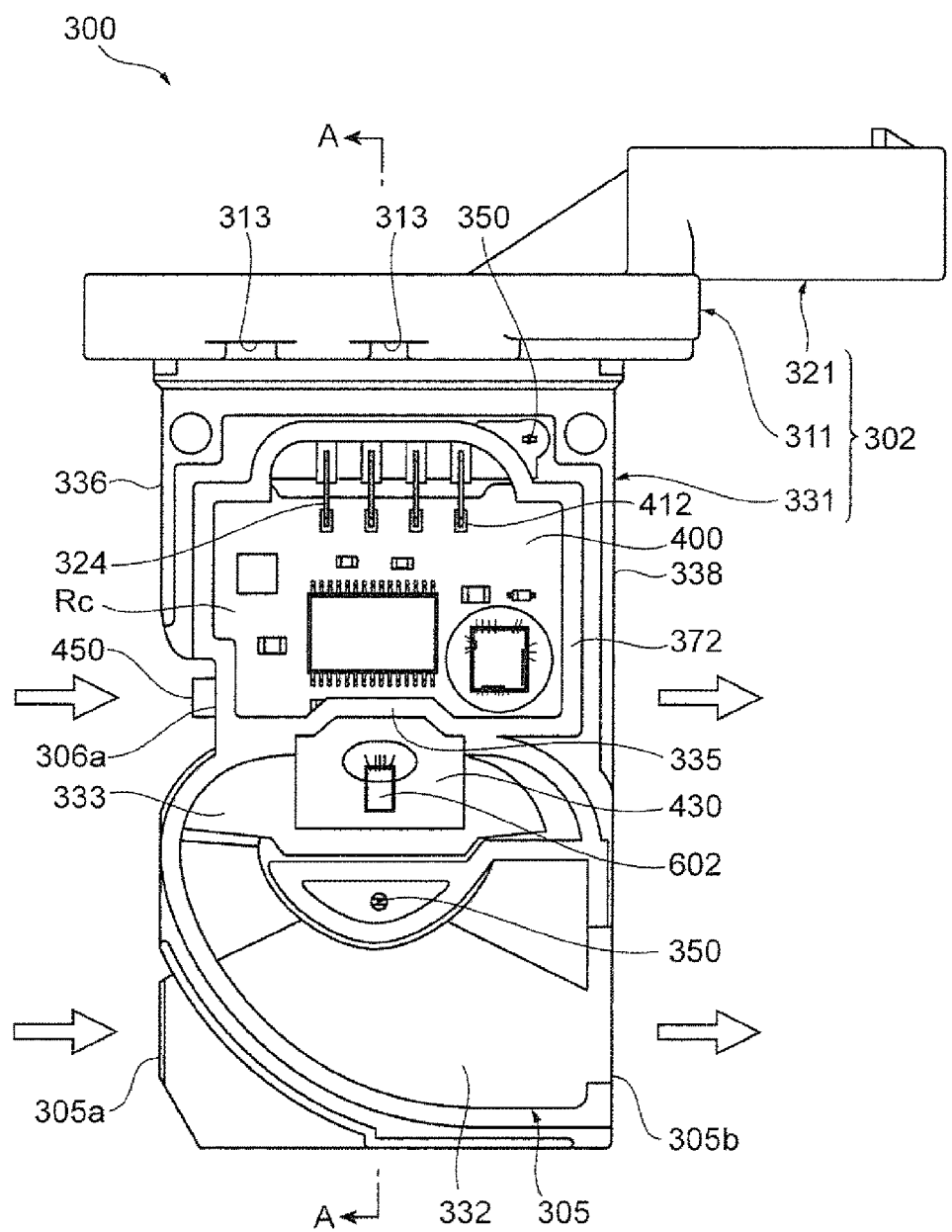
FIG. 7 is a front view illustrating a state in which a front cover is removed from the physical-quantity detection device.

A circuit substrate 400 is integrally provided in the measurement section 331 through insert-molding during molding of the housing 302 (refer to FIG. 7). At least one detection unit that detects the physical quantity of the gas to be measured 30 that flows through the main passage 124, and a circuit unit that processes a signal that is detected by the detection unit are provided in the circuit substrate 400. The detection unit is disposed at a position that is exposed to the gas to be measured 30, and the circuit unit is disposed in a circuit chamber that is hermetically closed by the front cover 303.

A sub-passage groove is formed in a front surface and a rear surface of the measurement section 331, and a first sub-passage 305 is formed in cooperation of the front cover 303 and the rear cover 304. A first sub-passage inlet 305a that takes a part of the gas to be measured 30 such as intake air into the first sub-passage 305, and a first sub-passage outlet 305b that allows the gas to be measured 30 to return to the main passage 124 from the first sub-passage 305 are provided at a front end of the measurement section 331. A part of the circuit substrate 400 protrudes in the middle of the passage of the first sub-passage 305. A flow rate detection unit 602 (refer to FIG. 7), which is a detection unit, is disposed at the protruding portion to detect a flow rate of the gas to be measured 30.

A second sub-passage 306, which a part of the gas to be measured 30 such as intake air is taken into a sensor chamber Rs, is provided at an intermediate portion of the measurement section 331 that is closer to the flange 311 in relation to the first sub-passage 305. The second sub-passage 306 is formed by cooperation of the measurement section 331 and the rear cover 304. The second sub-passage 306 includes a second sub-passage inlet 306a that is opened to an upstream side outer wall 336 to take in the gas to be measured 30, and a second sub-passage outlet 306b that is opened to a downstream side outer wall 338 so as to allow the gas to be measured 30 to return from the second sub-passage 306 to the main passage 124. The second sub-passage 306 communicates with the sensor chamber Rs that is formed on a rear surface side of the measurement section 331. A pressure sensor and a humidity sensor, which are provided on a rear surface of the circuit substrate 400 as a detection unit, are disposed in the sensor chamber Rs.

2.2 Effect Based on External Structure of Physical-Quantity Detection Device 300

In the physical-quantity detection device 300, the second sub-passage inlet 306a is provided at the central portion of the measurement section 331 that extends from the flange 311 toward a central direction of the main passage 124, and the first sub-passage inlet 305a is provided at the front end of the measurement section 331. Accordingly, it is possible to take a gas at a portion, which is closer to the central portion that is spaced away from an inner wall surface of the main passage 124, instead of the vicinity of the inner wall surface into the first sub-passage 305 and the second sub-passage 306, respectively. Accordingly, the physical-quantity detection device 300 can measure a physical quantity of a gas at a portion spaced away from the inner wall surface of the main passage 124, and thus it is possible to reduce an measurement error in the physical quantity which relates to heat or a decrease in a flow rate in the vicinity of the inner wall surface.

The measurement section 331 has a shape that longitudinally extends along an axis that faces the center from the outer wall of the main passage 124, and a width in a thickness direction is set to have a narrow shape as illustrated in FIG. 4 and FIG. 5. That is, in the measurement section 331 of the physical-quantity detection device 300, a width of a lateral surface is thin, and a front side has an approximately rectangular shape. According to this, the physical-quantity detection device 300 can include the first sub-passage 305 having a sufficient length, and can suppress fluid resistance to a small value with respect to the gas to be measured 30. Accordingly, the physical-quantity detection device 300 can suppress the fluid resistance to a small value, and can measure a flow rate of the gas to be measured 30 with high accuracy.

2.3 Structure and Effect of Flange 311

In the flange 311, a plurality of recesses 313 are provided in a lower surface 312 that faces the main passage 124. According to this, a heat transfer surface with the main passage 124 is reduced, and the physical-quantity detection device 300 is less likely to be affected by heat. In the physical-quantity detection device 300, the measurement section 331 is inserted into an inner side from an attachment hole provided in the main passage 124, and the lower surface 312 of the flange 311 faces the main passage 124. For example, the main passage 124 is an intake body, and the main passage 124 is maintained at a high temperature in many cases. In contrast, during starting at a cold area, it is considered that the main passage 124 is at a very low temperature. When the high-temperature or low-temperature state of the main passage 124 has an effect on measurement of various physical quantities, measurement accuracy decreases. In the flange 311, the recesses 313 are provided in the lower surface 312, and thus a space is formed between the lower surface 312 that faces the main passage 124, and the main passage 124. Accordingly, heat transfer from the main passage 124 to the physical-quantity detection device 300 is reduced, and thus it is possible to prevent deterioration of measurement accuracy due to heat.

Screw holes 314 of the flange 311 are used to fix the physical-quantity detection device 300 to the main passage 124, and a space is formed between a surface that faces the main passage 124 at the periphery of each of the screw holes 314, and the main passage 124 in order for the surface, which faces the main passage 124 at the periphery of the screw hole 314, to be spaced away from the main passage 124. According to this, it is possible to realize a structure in which heat transfer from the main passage 124 to the physical-quantity detection device 300 is reduced, and deterioration of measurement accuracy due to heat can be prevented.

2.4 Structure of External Connection Section 321

The external connection section 321 includes a connector 322 that is provided on an upper surface of the flange 311, and protrudes from the flange 311 toward a downstream side in a flow direction of the gas to be measured 30. An insertion hole 322a, into which a communication cable for connection with the control device 200 is inserted, is provided in the connector 322. As illustrated in FIG. 5, four external terminals 323 are provided on an inner side of the insertion hole 322a. The external terminals 323 serve as a terminal that outputs information of a physical quantity that is a measurement result of the physical-quantity detection device 300, and a power supply terminal that supplies DC power for operation of the physical-quantity detection device 300.

The connector 322 has a shape that protrudes from the flange 311 toward a downstream side of the flow direction of the gas to be measured 30, and is inserted from the downstream side to an upstream side of the flow direction. However, there is no limitation to this shape. For example, the connector 322 may have a shape that vertically protrudes from the upper surface of the flange 311, and is inserted along an extension direction of the measurement section 331. In addition, various changes can be made.

3. Overall Structure and Effect of Housing 3.1 Overall Structure of Housing 302

Next, description will be given of an overall structure of the housing 302 with reference to FIG. 7, FIGS. 8A to 8F, and FIG. 9. FIG. 7, and FIGS. 8A to 8F are views illustrating a state of the housing 302 in which the front cover 303 and the rear cover 304 are removed from the physical-quantity detection device 300. In the drawings, FIG. 7 is a front view of the housing 302, FIGS. 8A to 8F are rear views of the housing 302, and FIG. 9 is a cross-sectional view taken along line A-A in FIG. 7.

The housing 302 has a structure in which the measurement section 331 extends from the flange 311 toward the center of the main passage 124. The circuit substrate 400 is insert-molded on a base end side of the measurement section 331. The circuit substrate 400 is disposed in parallel along a surface of the measurement section 331 at an intermediate position between a front surface and a rear surface of the measurement section 331, and is integrally molded in the housing 302. The base end side of the measurement section 331 is partitioned into one side and the other side in a thickness direction.

A circuit chamber Rc, in which a circuit unit of the circuit substrate 400 is accommodated, is formed on a surface side of the measurement section 331, and a sensor chamber Rs, in which a pressure sensor 421 and a humidity sensor 422 are accommodated, is formed on a rear side of the measurement section 331. The circuit chamber Rc is hermetically closed by attaching the front cover 303 to the housing 302, and is completely isolated from an outer side. On the other hand, the sensor chamber Rs forms an inner space that communicates with an outer side of the measurement section 331 as a part of the second sub-passage 306 by attaching the rear cover 304 to the housing 302. A part of the circuit substrate 400 protrudes into the first sub-passage 305 from a partition wall 335 that separates the circuit chamber Rc of the measurement section 331 and the first sub-passage 305 from each other. A flow rate detection unit 602 is provided on a measurement flow path surface 430 of the protruding portion.

3.2 Structure of Sub-Passage Groove

A sub-passage groove configured to form the first sub-passage 305 is formed on a front end side in the longitudinal direction of the measurement section 331. The sub-passage groove configured to form the first sub-passage 305 includes a front surface side sub-passage groove 332 illustrated in FIG. 7, and a rear surface side sub-passage groove 334 illustrated in FIG. 8A. As illustrated in FIG. 7, the front surface side sub-passage groove 332 is gradually curved toward a flange 311 side that is a base end side of the measurement section 331 as it transitions toward the upstream side outer wall 336 from the first sub-passage outlet 305b that is opened to the downstream side outer wall 338 of the measurement section 331. The front surface side sub-passage groove 332 communicates with an opening 333 that passes through the measurement section 331 in a thickness direction thereof at a position in the vicinity of the upstream side outer wall 336. The opening 333 is formed along a flow direction of the gas to be measured 30 of the main passage 124 so as to extend between the upstream side outer wall 336 and the downstream side outer wall 338.

Figure 8A:
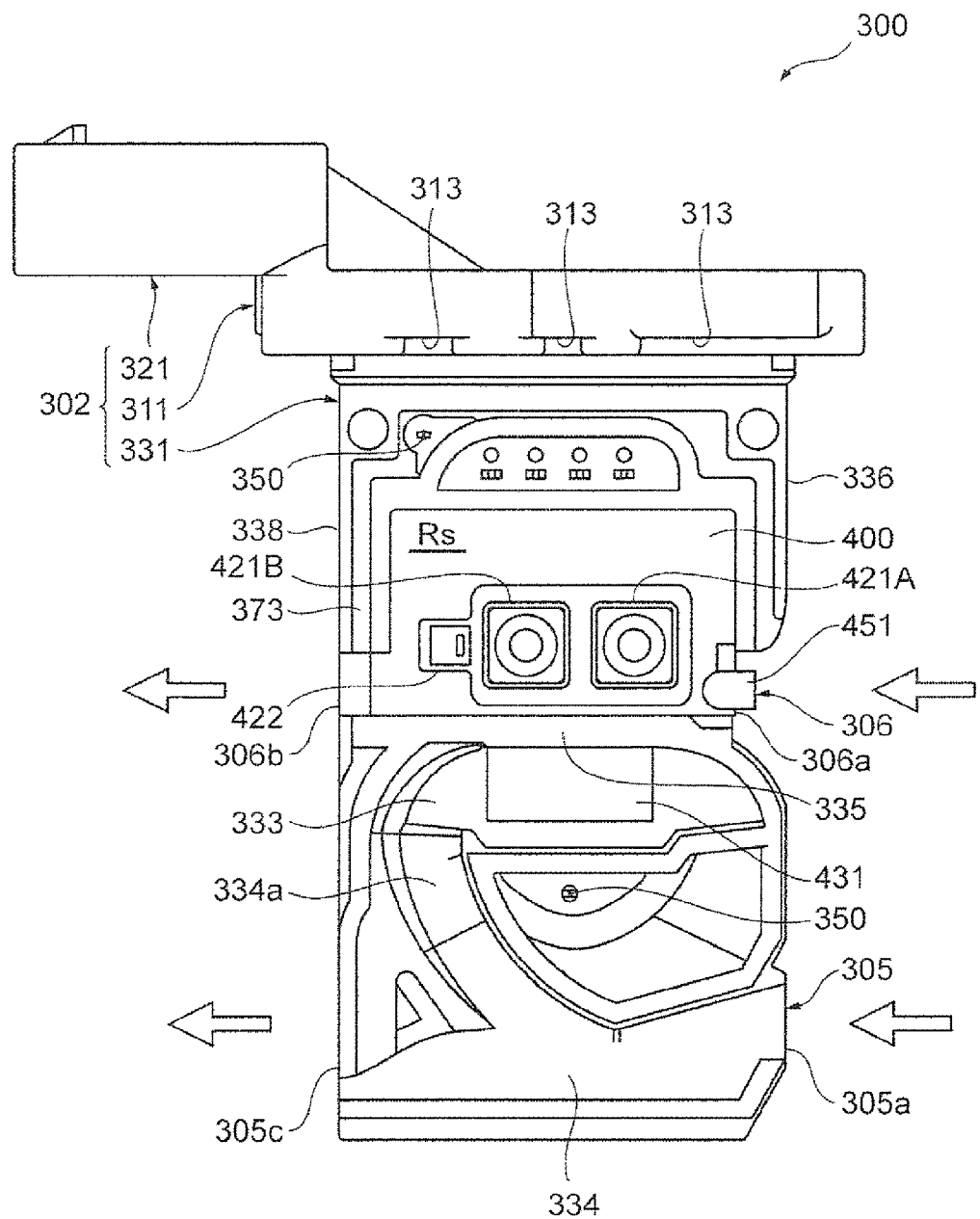
FIG. 8A is a rear view illustrating a state in which a rear cover is removed from the physical-quantity detection device.
Figure 9:
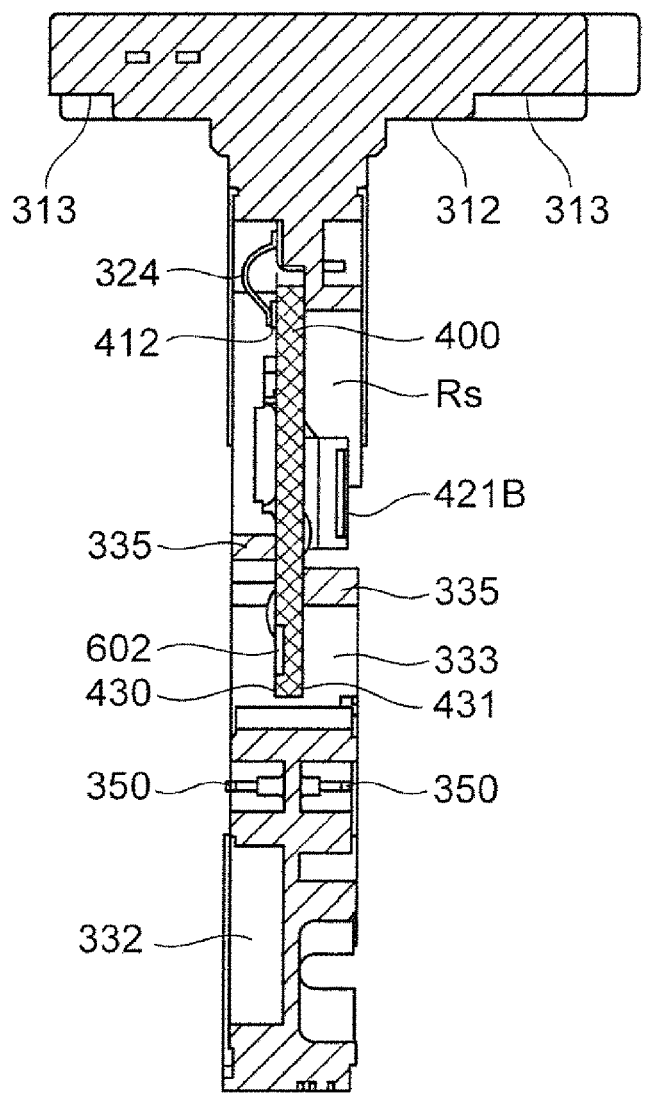
FIG. 9 is a view seen in a cross-sectional arrow direction along line A-A in FIG. 7.

As illustrated in FIG. 8A, the rear surface side sub-passage groove 334 transitions from the upstream side outer wall 336 toward the downstream side outer wall 338, and is divided into two parts at an intermediate position between the upstream side outer wall 336 and the downstream side outer wall 338. One of the two divided parts linearly extends as is as a discharge passage, and is opened to a discharge port 305c of the downstream side outer wall 338. The other part is gradually curved toward the flange 311 side that is the base end side of the measurement section 331 as it transitions to the downstream side outer wall 338, and communicates with the opening 333 at a position in the vicinity of the downstream side outer wall 338.

The rear surface side sub-passage groove 334 forms an inlet groove into which the gas to be measured 30 flows from the main passage 124, and the front surface side sub-passage groove 332 forms an outlet groove that allows the gas to be measured 30, which is taken-in from the rear surface side sub-passage groove 334, to return to the main passage 124. The front surface side sub-passage groove 332 and the rear surface side sub-passage groove 334 are provided at a front end of the housing 302, and thus it is possible to take in a gas at a portion spaced away from the inner wall surface of the main passage 124, in other words, a gas that flows through a portion close to the central portion of the main passage 124 as the gas to be measured 30. A gas, which flows through the vicinity of the inner wall surface of the main passage 124 is affected by a wall surface temperature of the main passage 124, and has a temperature that is different from an average temperature of a gas such as intake air that flows through the main passage 124 in many cases. In addition, the gas, which passes through the vicinity of the inner wall surface of the main passage 124, may has a flow rate that is slower than an average flow rate of a gas that flows through the main passage 124 in many cases. The physical-quantity detection device 300 of this example is less likely to be susceptible to the effect, and thus it is possible to suppress deterioration of measurement accuracy.

As illustrated in FIG. 8A, a part of the gas to be measured 30, which flows through the main passage 124, is taken into the rear surface side sub-passage groove 334 from the first sub-passage inlet 305a, and flows through the inside of the rear surface side sub-passage groove 334. In addition, a foreign substance with a large mass, which is included in the gas to be measured 30, flows into a discharge passage that linearly extends as is from a divergence in combination with apart of the gas to be measured, and is discharged from the discharge port 305c of the downstream side outer wall 338 to the main passage 124.

The rear surface side sub-passage groove 334 has a shape of which a depth increases as it transitions, and the gas to be measured 30 gradually moves to a front surface side of the measurement section 331 as the gas to be measured 30 flows along the rear surface side sub-passage groove 334. Particularly, a steeply inclined portion 334a of which a depth steeply increases in front of the opening 333 is provided in the rear surface side sub-passage groove 334, and thus a part of air with a small mass moves along the steeply inclined portion 334a, and flows through the measurement flow path surface 430 side of the circuit substrate 400 on an inner side of the opening 333. On the other hand, it is difficult for a foreign substance with a large mass to steeply change a route, and thus this foreign substance flows through a measurement flow-path-surface rear surface 431 side.

As illustrated in FIG. 7, the gas to be measured 30, which moves to a front surface side in the opening 333, flows along the measurement flow path surface 430 of the circuit substrate, and is subjected to heat transfer with the flow rate detection unit 602 that is provided on the measurement flow path surface 430. According to this, measurement of a flow rate is performed. Air, which flows into the front surface side sub-passage groove 332 from the opening 333, flows along the front surface side sub-passage groove 332, and is discharged to the main passage 124 from the first sub-passage outlet 305b that is opened to the downstream side outer wall 338.

A substance with a large mass such as dust, which is mixed in the gas to be measured 30, has a great inertial force, and thus it is difficult for the substance to steeply change a route to a groove depth direction along a surface of a part of the steeply inclined portion 334a of which a groove depth steeply increases. Accordingly, the foreign substrate with a large mass moves to the measurement flow-path-surface rear surface 431 side, and thus it is possible to suppress the foreign substance from passing through the vicinity of the flow rate detection unit 602. This example has a configuration in which the majority of the foreign substance with a large mass other than a gas is allowed to pass through the measurement flow-path-surface rear surface 431 that is a rear surface of the measurement flow path surface 430, and thus it is possible to reduce an effect of a contaminant due to a foreign substance such as an oily component, carbon, and dust. As a result, it is possible to suppress deterioration of measurement accuracy. That is, due to a shape in which a route of the gas to be measured 30 is steeply changed along an axis that intersects a flow axis of the main passage 124, it is possible to reduce an effect by a foreign substance that is mixed in the gas to be measured 30.

3.3 Structure and Effect of Second Sub-Passage and Sensor Chamber

The second sub-passage 306 is formed between the second sub-passage inlet 306a and the second sub-passage outlet 306b in parallel to the flange 311 to follow the flow direction of the gas to be measured 30. The second sub-passage inlet 306a is formed by cutting out apart of the upstream side outer wall 336, and the second sub-passage outlet 306b is formed by cutting out a part of the downstream side outer wall 338. Specifically, the second sub-passage inlet 306a and the second sub-passage outlet 306b are formed by cutting out a part of the upstream side outer wall 336 and a part of the downstream side outer wall 338 on a rear surface side of the measurement section 331 at a position that continuously follows an upper surface of the partition wall 335 (refer to FIG. 4 and FIG. 5). The second sub-passage inlet 306a and the second sub-passage outlet 306b are cut out to a deep position at which a step difference with the rear surface of the circuit substrate 400 is not present. Since the gas to be measured 30 passes through the second sub-passage 306 along a rear surface of a substrate main body 401 of the circuit substrate 400, the second sub-passage 306 functions as a cooling channel that cools down the substrate main body 401. The circuit substrate 400 includes an LSI and a microcomputer that generates heat in many cases. Accordingly, the heat is transferred to the rear surface of the substrate main body 401, and the heat may be radiated by the gas to be measured 30 that passes through the second sub-passage 306.

The second sub-passage 306 includes the sensor chamber Rs in the middle of the flow path thereof. The sensor chamber Rs is formed to be expanded to the flange 311 side in relation to the second sub-passage inlet 306a and the second sub-passage outlet 306b, that is, to broaden toward the base end side of the measurement section 331 from the partition wall 335. A pressure of the gas to be measured 30, which flows into the second sub-passage 306 from the second sub-passage inlet 306a, is detected by the pressure sensor 421 in the sensor chamber Rs, and relative humidity and a temperature thereof are detected by the humidity sensor 422. A plurality of pieces of information of the temperature, the relative humidity, and the pressure are necessary to calculate a mixing ratio that is used for a fuel control. It is preferable that the sensors are disposed in the same sensor chamber Rs at positions adjacent to each other so as to measure the mixing ratio with high accuracy. According to this, it is possible to improve detection accuracy of the sensors.

The pressure sensor 421 and the humidity sensor 422 are less likely to be affected by the flow of the gas to be measured 30 in comparison to the flow rate detection unit 602. Particularly, the humidity sensor 422 may employ any configuration as long as a diffusion level of moisture in the gas to be measured 30 can be secured. Accordingly, the pressure sensor 421 and the humidity sensor 422 can be provided in the second sub-passage 306 that linearly extends along the flow direction of the gas to be measured 30. In contrast, in the flow rate detection unit 602, a flow rate is demanded to be equal to or greater than any constant flow rate, it is necessary to be kept away from dust or a contaminant, and it is necessary to consider an effect with respect to pulsation. Accordingly, the flow rate detection unit 602 is provided in the first sub-passage 305 having a shape that orbits in a loop shape.

FIG. 8A illustrates an example of the humidity sensor 422 and the pressure sensor 421. The humidity sensor 422 and the pressure sensor 421 are disposed in a row to be parallel to each other along the flow direction of the gas to be measured 30 that passes through the second sub-passage 306, and the pressure sensor 421 is disposed upstream of the humidity sensor 422. In the pressure sensor 421, two pressure sensors 421A and 421B are disposed in a row to be parallel to each other along the flow direction of the gas to be measured 30 in the second sub-passage 306, and the humidity sensor 422 is disposed downstream of the two pressure sensors 421A and 421B.

The two pressure sensors 421A and 421B have an external shape that is greater than that of the humidity sensor 422, and an projection area of the pressure sensors 421A and 421B in the second sub-passage 306 in the flow direction of the gas to be measured 30 is set to be greater than that of the humidity sensor 422. In contrast, a projection area of the humidity sensor 422 in the flow direction of the gas to be measured 30 is set to be smaller than that of the pressure sensors 421A and 421B, and is disposed at a position that enters a range of the projection area of the pressure sensors 421A and 421B. Accordingly, the humidity sensor 422 is set to be shielded by the pressure sensors 421A and 421B in the flow direction of the gas to be measured 30.

In this manner, in the sensor chamber Rs, the pressure sensors 421A and 421B having a relatively large external shape are disposed on an upstream side, and the humidity sensor 422 having a relatively small external shape is disposed downstream of the pressure sensors 421A and 421B. Accordingly, a water droplet or a contaminant, which flows in in combination with the gas to be measured 30, adheres to the pressure sensors 421A and 421B. In addition, the flow of the gas to be measured 30 is changed into a direction to be separated from the circuit substrate 400 by the pressure sensors 421A and 421B. According to this, direct hitting of the gas to be measured 30 to the humidity sensor 422 can be obstructed.

Accordingly, in a case where a water droplet and a contaminant are included in the gas to be measured 30 that passes through the second sub-passage 306, it is possible to suppress adherence of the water droplet and the contaminant to the humidity sensor 422. According to this, it is possible to protect the humidity sensor 422 that has lower tolerance to the water droplet and the contaminant in comparison to the pressure sensor 421. As a result, it is possible to accurately measure humidity.

FIG. 8B to FIG. 8E are views illustrating other examples of the humidity sensor and the pressure sensor. Furthermore, the same reference numeral will be given to the same constituent element as in FIG. 8A, and detailed description thereof will not be repeated.

Figure 8B:
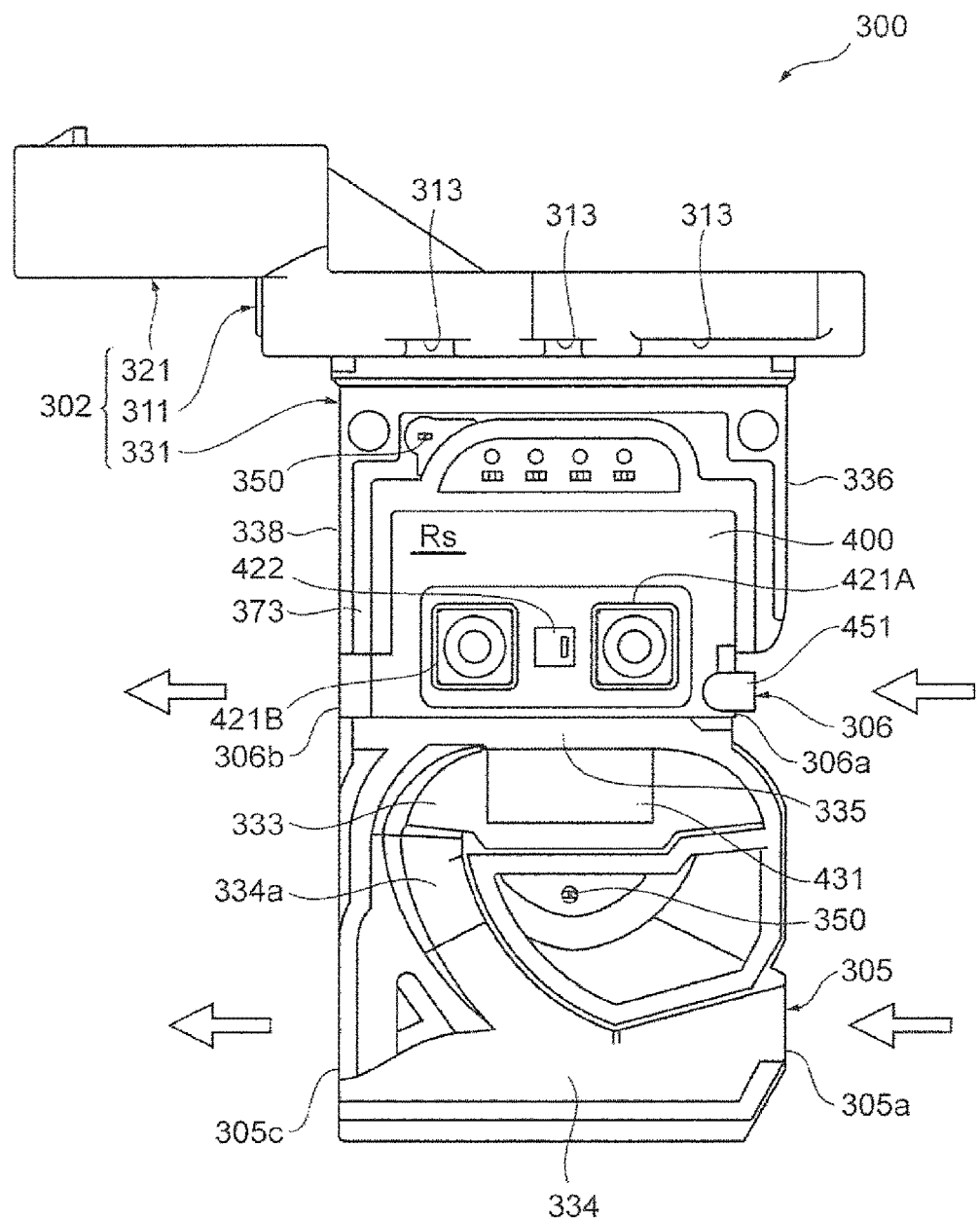
FIG. 8B is a rear view illustrating another example.

In an example illustrated in FIG. 8B, the pressure sensors 421A and 421B are respectively disposed upstream of the humidity sensor 422 and downstream of the humidity sensor 422. That is, the pressure sensors 421A and 421B are disposed on an upstream side and a downstream side in the flow direction of the gas to be measured 30 with the humidity sensor 422 interposed therebetween. Accordingly, in addition to the upstream side of the second sub-passage 306, the humidity sensor 422 is also shielded from the gas to be measured 30 that flows backward on a downstream side of the second sub-passage 306 due to pulsation and the like in the main passage. Accordingly, it is possible to prevent the gas to be measured 30, which flows backward, from directly hitting to the humidity sensor 422. Accordingly, it is also possible to suppress pour water of a water droplet contained in the gas to be measured 30, and it is possible to suppress adhesion of a contaminant such as dust to the humidity sensor 422.

Figure 8C:
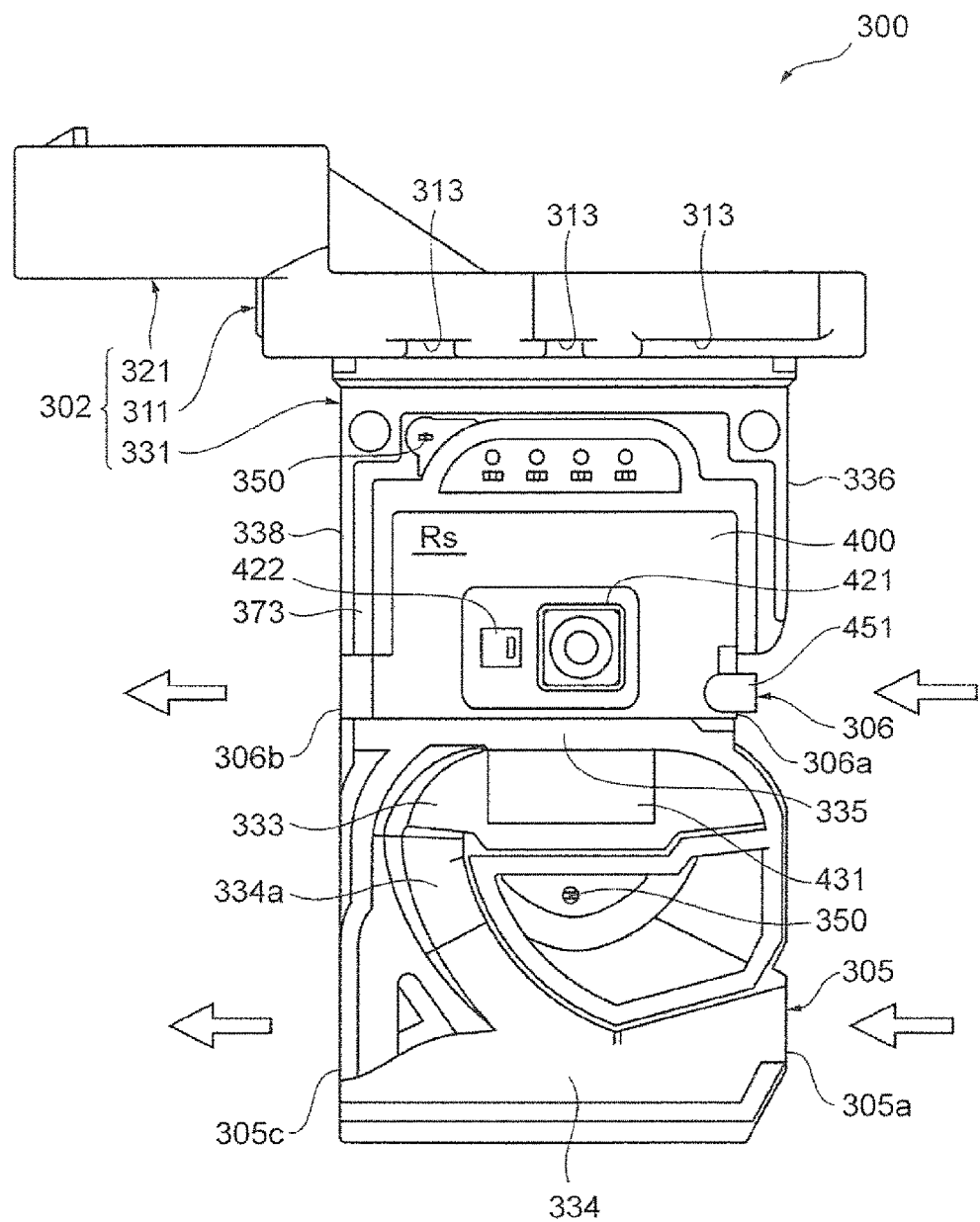
FIG. 8C is a rear view illustrating still another example.

In an example illustrated in FIG. 8C, only one of the pressure sensor 421 is disposed upstream of the humidity sensor 422. Even in this case, as is the case with the example illustrated in FIG. 8A, the humidity sensor 422 is shielded by the pressure sensor 421, and thus it is possible to prevent the gas to be measured 30 from directly hitting to humidity sensor 422. Accordingly, it is possible to suppress adhesion of a water droplet or a contaminant to the humidity sensor 422, and thus it is possible to protect the humidity sensor 422.

Figure 8D:
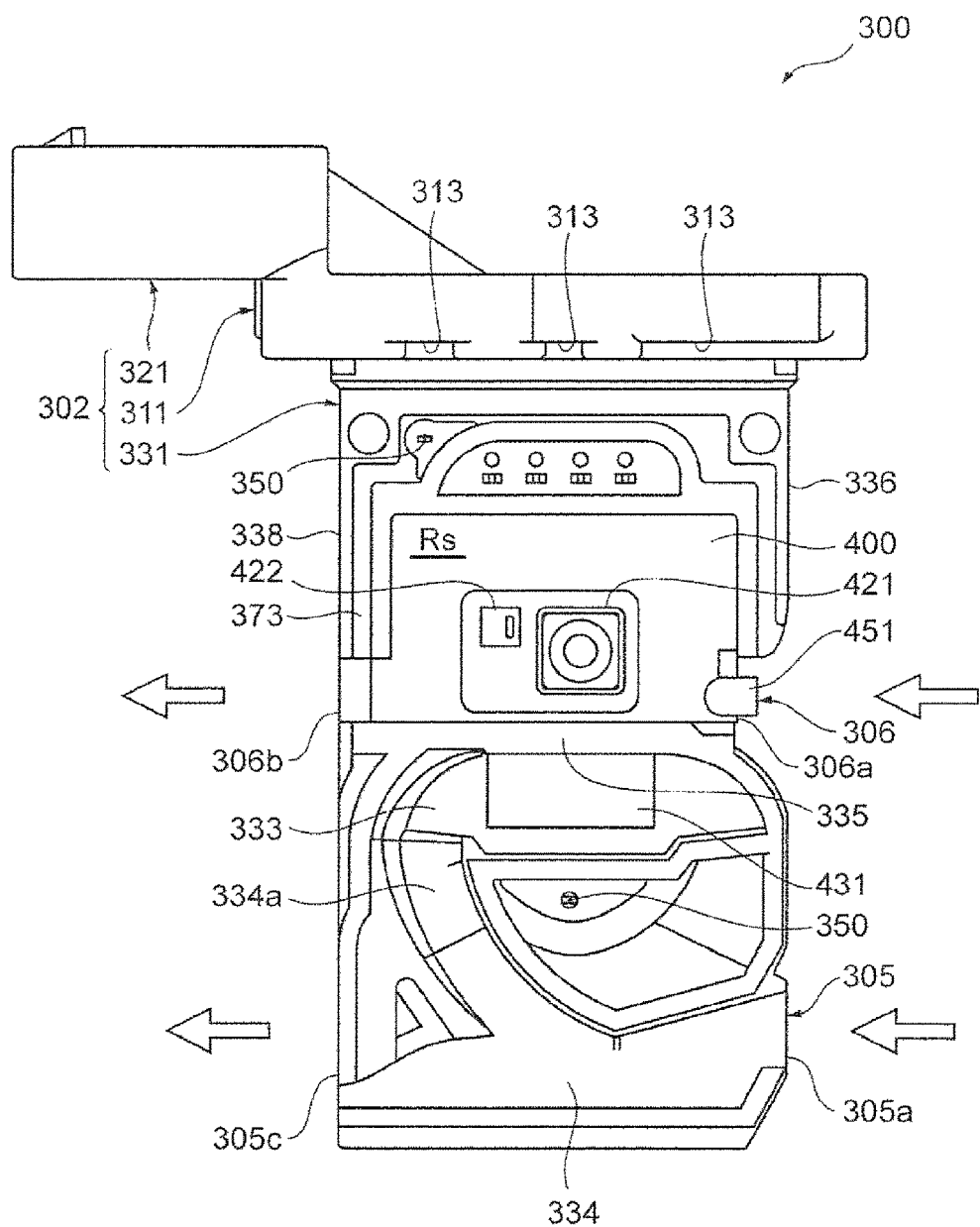
FIG. 8D is a rear view illustrating still another example.

In an example illustrated in FIG. 8D, a relative position between the humidity sensor 422 and the pressure sensor 421 is different from FIG. 8C, and the humidity sensor 422 is disposed downstream of the pressure sensor 421 in a state in which the centers are offset from each other. Specifically, in the example illustrated in FIG. 8C, the central positions are disposed to be positioned on the same straight line along the flow direction of the gas to be measured 30. However, in FIG. 8D, the humidity sensor 422 is disposed to further shift toward the flange 311 side in comparison to the pressure sensor 421, that is, to further shift toward the base end side of the measurement section 331. Furthermore, even in this example, the humidity sensor 422 is disposed at a position that enters a range of the projection area of the pressure sensor 421 along the flow direction of the gas to be measured 30, and is shielded by the pressure sensor 421. The humidity sensor 422 is disposed at a position that deviates from a straight line that connects the second sub-passage inlet 306a and the second sub-passage outlet 306b, and shifts toward the flange 311 side. The humidity sensor 422 is further less likely to be susceptible to direct hitting of the gas to be measured 30, and is further protected from a water droplet or a contaminant.

Figure 8E:
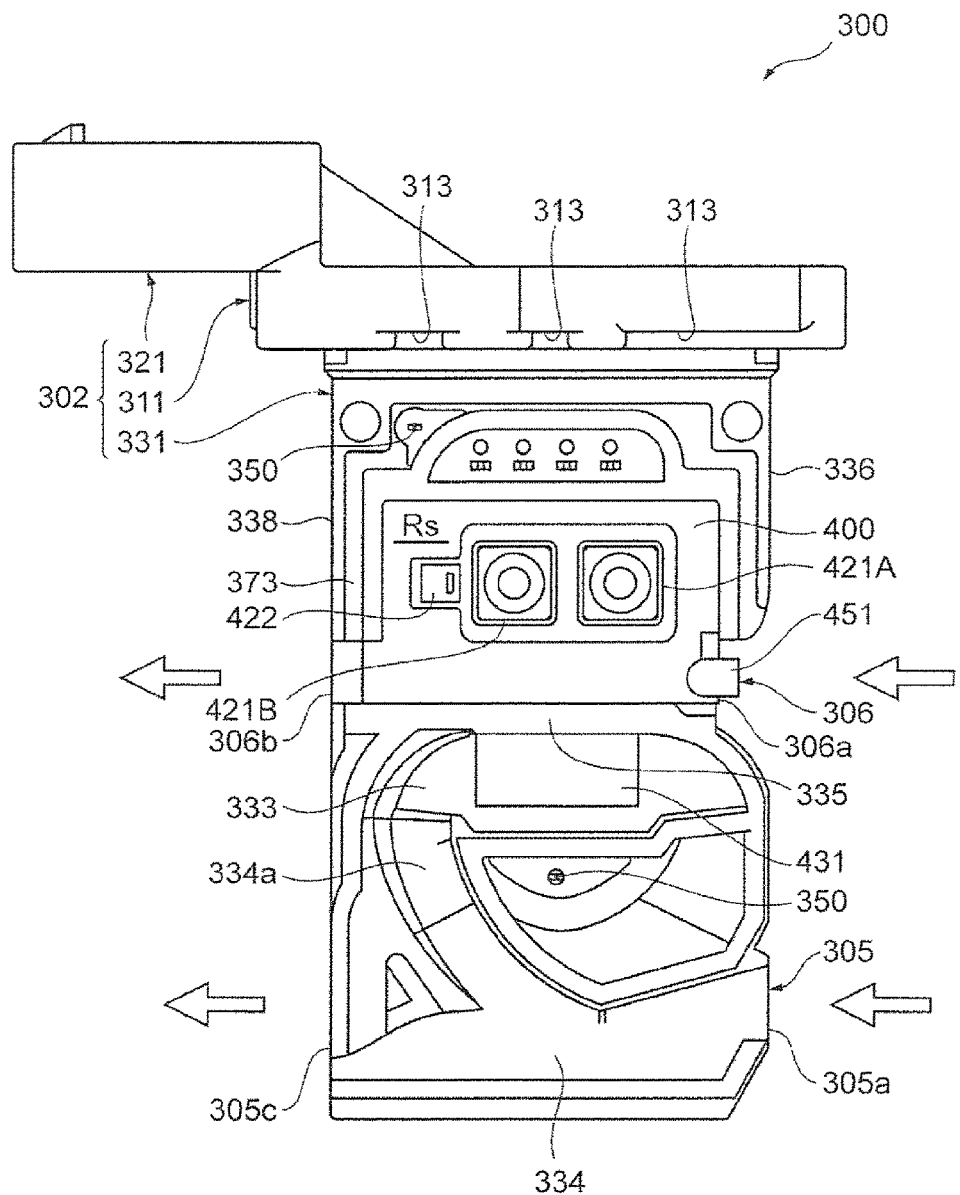
FIG. 8E is a rear view illustrating still another example.

In an example illustrated in FIG. 8E, the two pressure sensors 421A and 421B, and the humidity sensor 422 are disposed at a position that is offset from the straight line that connects the second sub-passage inlet 306a and the second sub-passage outlet 306b toward the flange 311 side. Accordingly, it is possible to reduce an effect of a dynamic pressure of the gas to be measured 30 that passes through the second sub-passage 306, and it is possible to improve detection accuracy of the pressure sensors 421A and 421B. In addition, for example, in a case where the physical-quantity detection device 300 is mounted in the intake air passage in a posture state in which the front side of the measurement section 331 faces a downward side, since the two pressure sensors 421A and 421B, and the humidity sensor 422 are disposed on an upward side of the straight line that connects the second sub-passage inlet 306a and the second sub-passage outlet 306b, it is possible to suppress adhesion of a contaminant or a water droplet.

3.4 Shape and Effect of Front Cover 303 and Rear Cover 304

FIGS. 10(a) and 10(b) are views illustrating an external appearance of the front cover 303. In the drawing, FIG. 10(a) is a front view, and FIG. 10(b) is a cross-sectional view taken along line B-B in FIG. 10(a). FIG. 11 is a view illustrating an external appearance of the rear cover 304. In the drawing, FIG. 11(a) is a front view, and FIG. 11 (b) is a cross-sectional view taken along line B-B in FIG. 11 (a).

Figure 10:
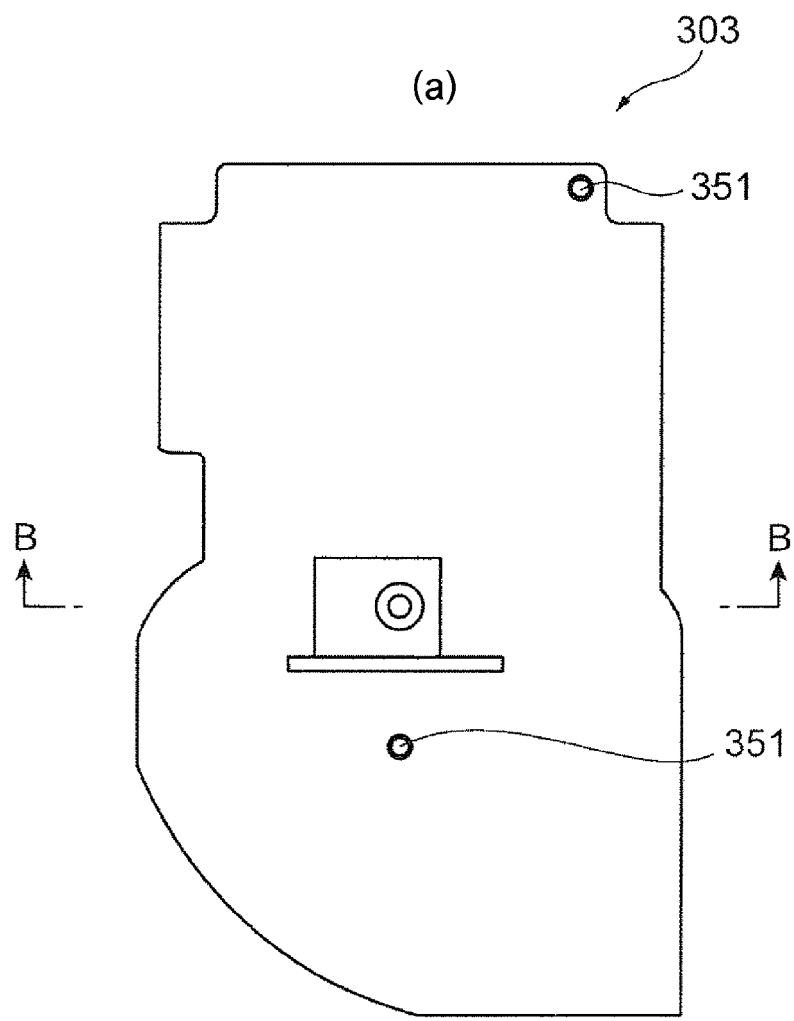
FIGS. 10(a) and 10(b) are views illustrating a configuration of the front cover.
Figure 10:
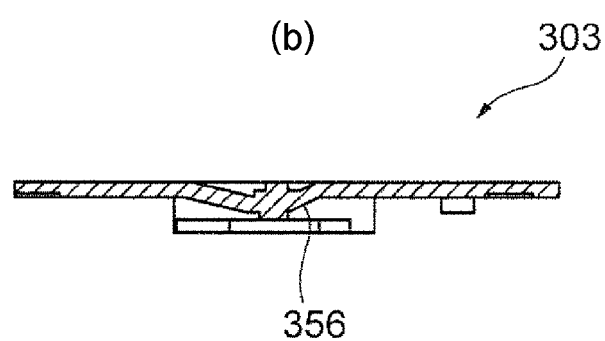
Figure 11:
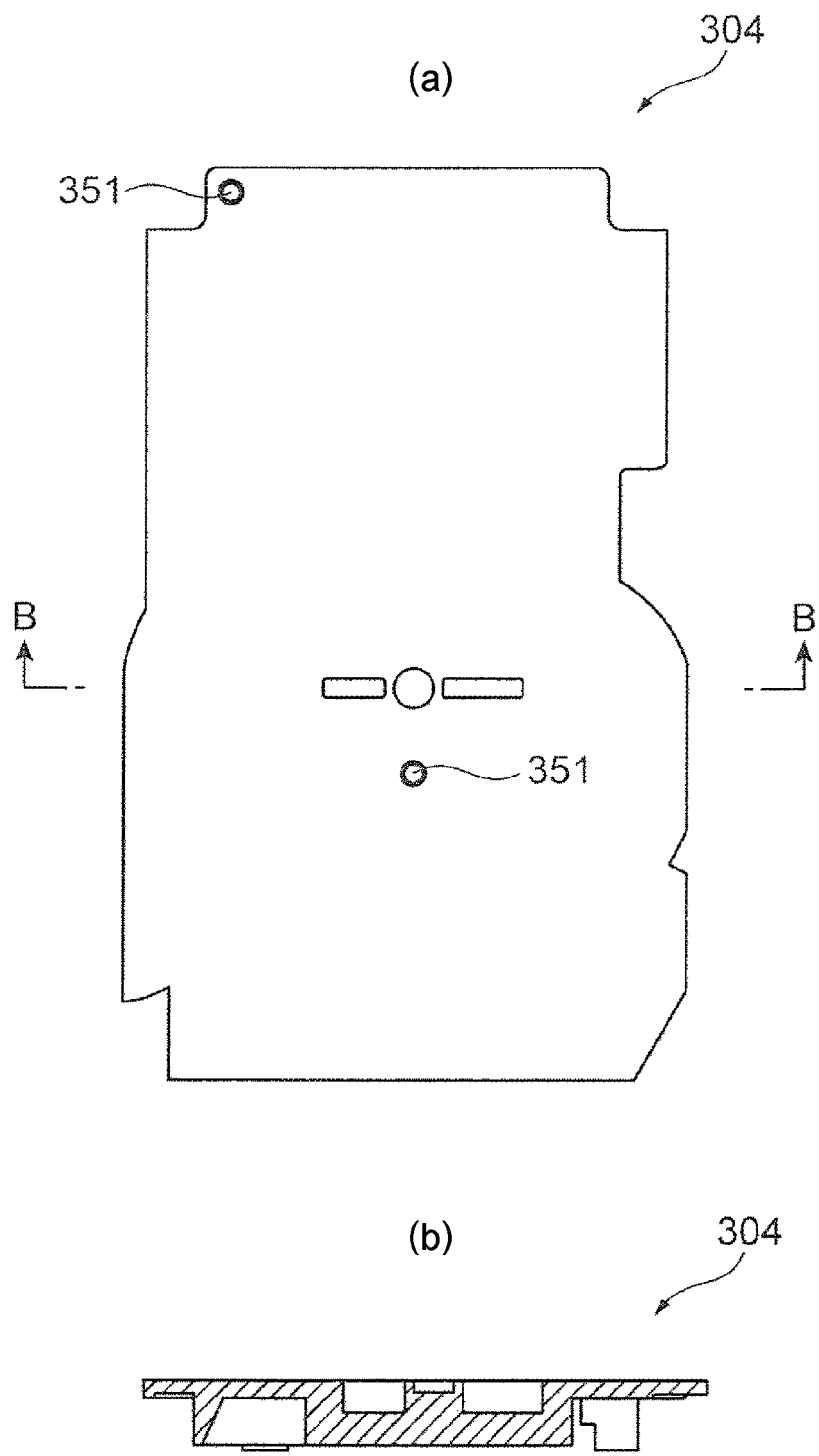
FIGS. 11(a) and 11(b) are views illustrating a configuration of the rear cover.

In FIGS. 10 (a) and 10 (b) and FIGS. 11 (a) and 11 (b), the front cover 303 and the rear cover 304 respectively cover the front surface side sub-passage groove 332 and the rear surface side sub-passage groove 334 of the housing 302 to form the first sub-passage 305. In addition, the front cover 303 forms the circuit chamber Rc that is hermetically closed, and the rear cover 304 closes a rear surface side concave portion of the measurement section 331 to form the second sub-passage 306 and the sensor chamber Rs that communicates with the second sub-passage 306.

The front cover 303 includes a protrusion 356 at a position that faces the flow rate detection unit 602, and is also used to form a diaphragm between the front cover 303 and the measurement flow path surface 430. Accordingly, it is preferable that molding accuracy is high. The front cover 303 and the rear cover 304 are manufactured by a resin molding process in which a thermoplastic resin is injected into a mold, and thus the front cover 303 and the rear cover 304 can be manufactured with high molding accuracy.

The front cover 303 and the rear cover 304 are provided with a plurality of fixing holes 351 into which a plurality of fixing pins 350 are inserted from the measurement section 331. The front cover 303 and the rear cover 304 are respectively formed on the front surface and the rear surface of the measurement section 331, and at this time, positioning of the front cover 303 and the rear cover 304 is established by inserting the fixing pins 350 into the fixing holes 351. In addition, the front cover 303 and the rear cover 304 are joined to edges of the front surface side sub-passage groove 332 and the rear surface side sub-passage groove 334 through laser welding and the like. Similarly, the front cover 303 and the rear cover 304 are joined to edges of the circuit chamber Rc and the sensor chamber Rs through laser welding and the like.

3.5 Fixing Structure of Circuit Substrate 400 by Housing 302, and Effect Thereof Next, description will be given of fixing of the circuit substrate 400 through a resin molding process with respect to the housing 302. The circuit substrate 400 is integrally molded in the housing 302 so that the flow rate detection unit 602 of the circuit substrate 400 is disposed at a predetermined location of the sub-passage groove that forms the sub-passage, for example, in this embodiment, at the opening 333 that is a connection portion between the front surface side sub-passage groove 332 and the rear surface side sub-passage groove 334.

Portions, at which an outer peripheral edge of a base portion 402 of the circuit substrate 400 is embedded in the housing 302 through resin molding, are provided in the measurement section 331 of the housing 302 as fixing portions 372 and 373. The fixing portions 372 and 373 fix the outer peripheral edge of the base portion 402 of the circuit substrate 400 by interposing the outer peripheral edge between the front surface side and the rear surface side.

The housing 302 is manufactured in a resin molding process. In the resin molding process, the circuit substrate 400 is embedded in a resin of the housing 302, and is fixed in the housing 302 through resin molding. In this configuration, the flow rate detection unit 602 can maintain a positional relationship, a directional relationship, and the like which are relationships with a sub-passage in which the flow rate detection unit 602 performs heat transfer with the gas to be measured 30 to measure a flow rate, for example, the front surface side sub-passage groove 332 or the rear surface side sub-passage groove 334 with very high accuracy, and it is possible to suppress an error or a deviation which occurs for each circuit substrate 400 to a very small value. As a result, it is possible to greatly improve measurement accuracy of the circuit substrate 400. For example, it is possible to significantly improve the measurement accuracy in comparison to a method in which the fixing is performed by using an adhesive in the related art.

The physical-quantity detection device 300 may be produced through mass production, and there is a limit for an improvement in the measurement accuracy in the method in which bonding is performed with an adhesive while strictly performing measurement. However, when the sub-passage is molded in the resin molding process in which the sub-passage through which the gas to be measured 30 flows is formed, and the circuit substrate 400 is fixed simultaneously with the molding similar to this example, it is possible to greatly reduce a deviation in the measurement accuracy, and it is possible to greatly improve the measurement accuracy of the physical-quantity detection device 300.

For example, in the example illustrated in FIG. 7 and FIG. 8A, it is possible to fix the circuit substrate 400 to the housing 302 with high accuracy for establishment of a defined relationship between the front surface side sub-passage groove 332, the rear surface side sub-passage groove 334, and the flow rate detection unit 602. According to this, in the physical-quantity detection device 300 that is produced through mass production, it is possible to normally obtain relationships such as a positional relationship and a shape relationship between the flow rate detection unit 602 of the circuit substrate 400 and the first sub-passage 305 with very high accuracy.

For example, in the first sub-passage 305 in which the flow rate detection unit 602 of the circuit substrate 400 is disposed in a fixed manner, for example, the front surface side sub-passage groove 332 and the rear surface side sub-passage groove 334 can be molded with very high accuracy, and thus a process of molding the first sub-passage 305 from the sub-passages grooves 332 and 334 is a process of covering both surfaces 17 of the housing 302 with the front cover 303 and the rear cover 304. This process is very simple, and is a process in which a factor that deteriorates the measurement accuracy is small. In addition, the front cover 303 and the rear cover 304 are produced by a resin molding process in which molding accuracy is high. Accordingly, it is possible to complete the sub-passage which is provided in a defined relationship with the flow rate detection unit 602 of the circuit substrate 400 with high accuracy. According to this method, high productivity is obtained in addition to the improvement in the measurement accuracy.

In contrast, in the related art, after a sub-passage is manufactured, and a measurement section is bonded to the sub-passage with an adhesive to produce a thermal type flowmeter. In the method of using the adhesive, a deviation in the thickness of the adhesive is great, and a bonding position or a bonding angle is different in each product. Therefore, there is a limit for an improvement in the measurement accuracy. In addition, in a case of performing the process with a mass production process, it is very difficult to improve the measurement accuracy.

In the example according to the invention, fixing of the circuit substrate 400 is performed through resin molding, and the sub-passage groove for molding of the first sub-passage 305 through the resin molding is molded simultaneously with the fixing. According to this configuration, the shape of the sub-passage groove becomes very accurate, and it is possible to fix the flow rate detection unit 602 in the sub-passage groove with very high accuracy.

A portion that relates to measurement of a flow rate, for example, the flow rate detection unit 602 or the measurement flow path surface 430 in which the flow rate detection unit 602 is formed is provided on a front surface of the circuit substrate 400. The flow rate detection unit 602 and the measurement flow path surface 430 are exposed from a resin that is used to mold the housing 302. That is, the flow rate detection unit 602 and the measurement flow path surface 430 are not covered with the resin that is used to mold the housing 302. The flow rate detection unit 602 of the circuit substrate 400 and the measurement flow path surface 430 are used as is even after resin molding of the housing 302, and are used for flow rate measurement in the physical-quantity detection device 300. According to this, the measurement accuracy is improved.

In the example according to the invention, the circuit substrate 400 is integrally molded in the housing 302, and the circuit substrate 400 is fixed to the housing 302 including the first sub-passage 305, and thus it is possible to reliably fix the circuit substrate 400 to the housing 302. Particularly, the protrusion 403 of the circuit substrate 400 is configured to protrude to the first sub-passage 305 through the partition wall 335, and thus sealing properties between the first sub-passage 305 and the circuit chamber Rc are high, and the gas to be measured 30 is prevented from being leaked from the first sub-passage 305 to the circuit chamber Rc, and circuit components, wirings, and the like of the circuit substrate 400 are prevented from coming into contact with the gas to be measured 30, and being corroded.

4. External Appearance of Circuit Substrate 400

4.1 Molding of Measurement Flow Path Surface 430 Provided with Flow Rate Detection Unit 602.

FIG. 12 to FIG. 15 illustrate an external appearance of the circuit substrate 400. Furthermore, an oblique line portion in the external appearance of the circuit substrate 400 indicates a fixing surface 432 and a fixing surface 434 on which the circuit substrate 400 is covered with a resin and is fixed with the resin when molding the housing 302 in the resin molding process.

Figure 12:
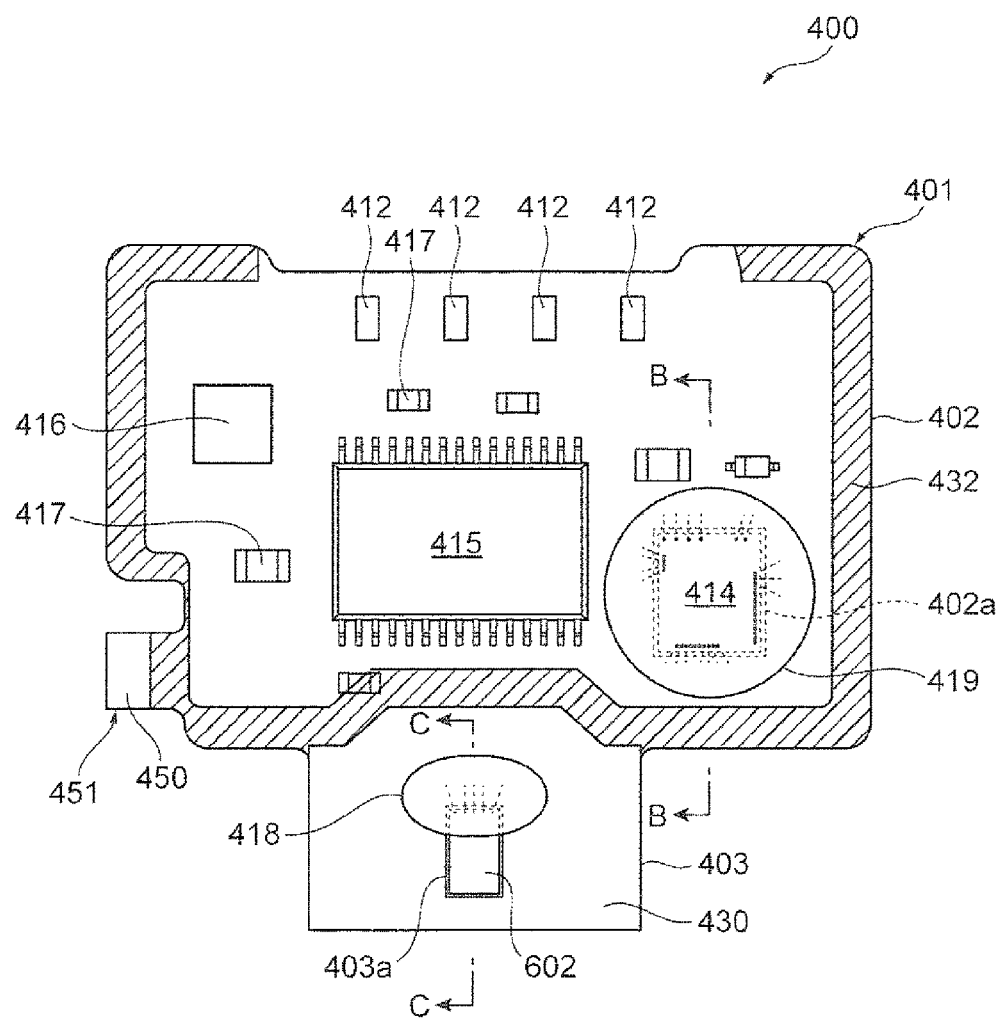
FIG. 12 is a front view of a circuit substrate.
Figure 13:
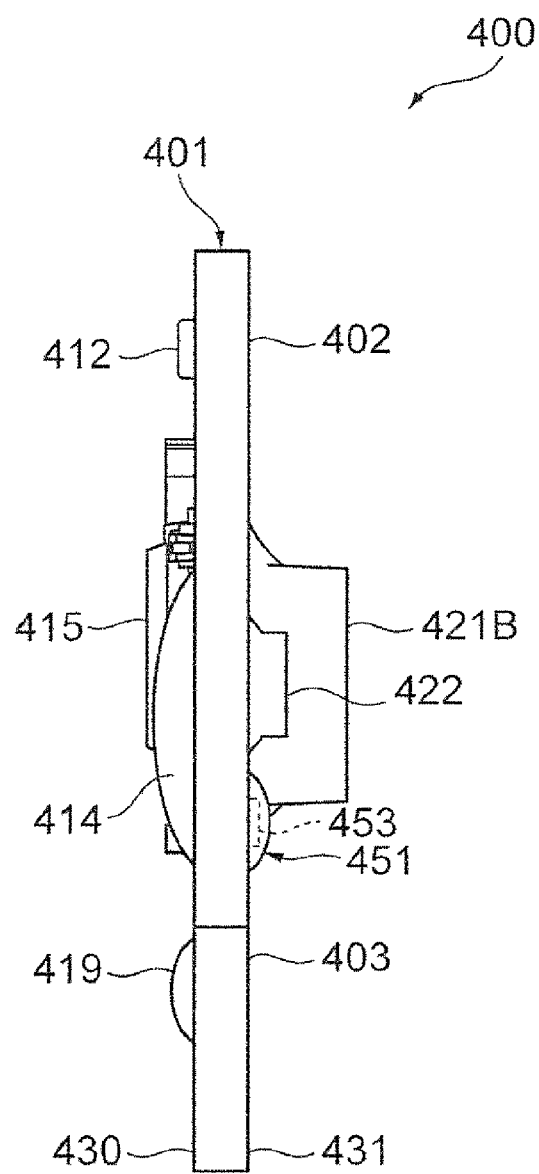
FIG. 13 is a right side view of the circuit substrate.
Figure 14:
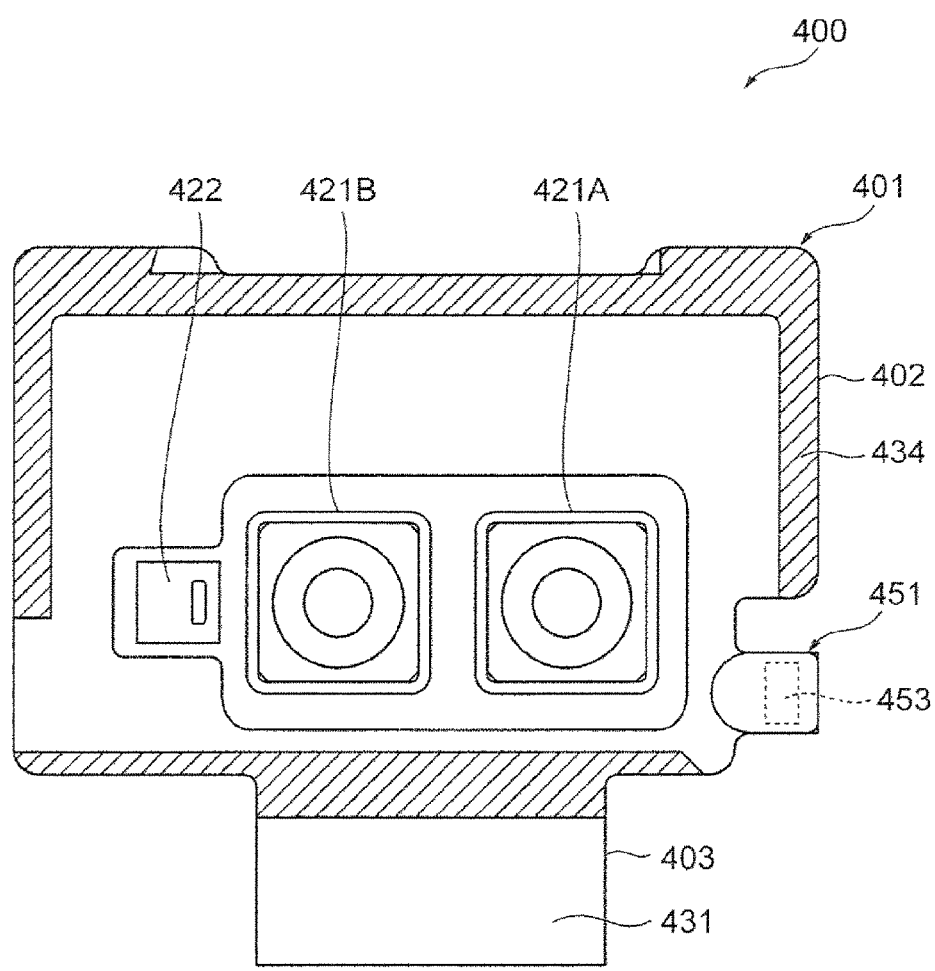
FIG. 14 is a rear view of the circuit substrate.
Figure 15:
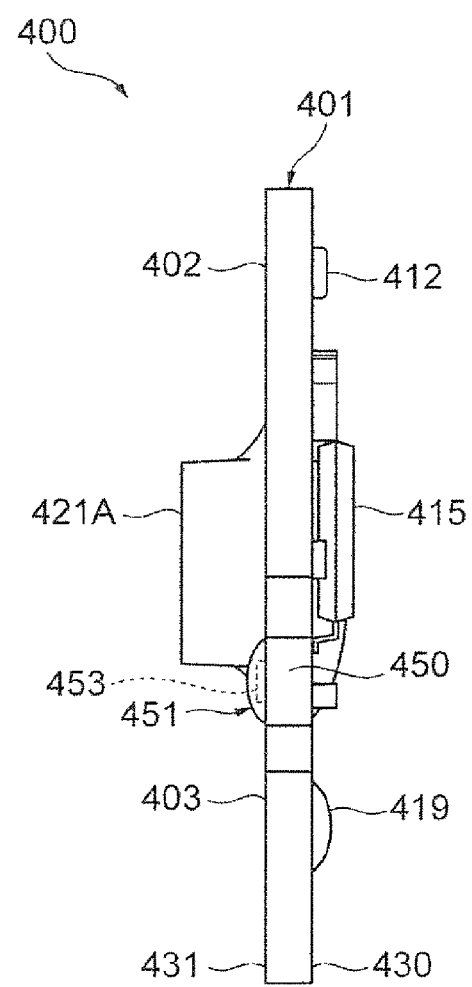
FIG. 15 is a left side view of the circuit substrate.

FIG. 12 is a front view of the circuit substrate, FIG. 13 is a right side view of the circuit substrate, FIG. 14 is a rear view of the circuit substrate, and FIG. 15 is a left side view of the circuit substrate.

The circuit substrate 400 includes the substrate main body 401, a circuit unit and the flow rate detection unit 602 that is a sensing element are provided on a front surface of the substrate main body 401, and the pressure sensor 421 and the humidity sensor 422 which are sensing elements are provided on a rear surface of the substrate main body 401. The substrate main body 401 is constituted by a glass epoxy resin material, and has a coefficient of thermal expansion that is closer to that of a thermoplastic resin that is used to mold the housing 302 in relation to a ceramic material. Accordingly, it is possible to reduce a stress due to a difference in a coefficient of thermal expansion during insert molding into the housing 302, and it is possible to reduce deformation of the circuit substrate 400

The substrate main body 401 has a flat plate shape having a constant thickness. The substrate main body 401 has an approximately T-shape in a plan view, and includes a base portion 402 having an approximately rectangular shape, and a protrusion 403 that protrudes from one side of the base portion 402 and has an approximately rectangular shape in a size smaller than that of the base portion 402. The circuit unit is provided on a surface of the base portion 402. The circuit unit has a configuration in which electronic components such as an LSI 414, a microcomputer 415, a power supply regulator 416, and a chip component 417 such as a resistor and a capacitor are mounted on a circuit wiring (not illustrated). The amount of heat generation in the power supply regulator 416 is greater in comparison to other electronic components such as the microcomputer 415 and the LSI 414, and thus the power supply regulator 416 is disposed on a relatively upstream side in the circuit chamber Rc. The entirety of the LSI 414 including a metal wire such as an aluminum wire and a gold wire is sealed with a synthetic resin material 419, and thus handling properties of the circuit substrate 400 during insert molding are improved.

The protrusion 403 is disposed in the first sub-passage 305 during insert molding of the circuit substrate 400 in the housing 302, and the measurement flow path surface 430 that is a surface of the protrusion 403 extends along the flow direction of the gas to be measured 30. The flow rate detection unit 602 is provided on the measurement flow path surface 430 of the protrusion 403. The flow rate detection unit 602 performs heat transfer with the gas to be measured 30, measures a state of the gas to be measured 30, for example, a flow rate of the gas to be measured 30, and outputs an electrical signal indicating the flow rate in the main passage 124. It is preferable that a gas flows through the vicinity of the measurement flow path surface 430 is a laminar flow, and a turbulent flow is small in order for the flow rate detection unit 602 to measure the state of the gas to be measured 30 with high accuracy. Accordingly, it is preferable that a surface of the flow rate detection unit 602 and the measurement flow path surface 430 have no step difference, or the step difference is equal to or less than a predetermined value.

A concave portion 403a is formed in the surface of the measurement flow path surface 430, and the flow rate detection unit 602 is fit into the concave portion 403a. The concave portion 403a can be formed by performing laser machining. The concave portion 403a has a depth at which the surface of the flow rate detection unit 602 and the measurement flow path surface 430 have no step difference. The flow rate detection unit 602 and a wiring portion thereof are covered with a synthetic resin material 418 to prevent occurrence of electrolytic corrosion due to adherence of salt water.

Two pressure sensors 421A and 421B, and one humidity sensor 422 are provided on the rear surface of the substrate main body 401. The two pressure sensors 421A and 421B are disposed in a row on an upstream side and on a downstream side, respectively. In addition, the humidity sensor 422 is disposed downstream of the pressure sensor 421B. The two pressure sensors 421A and 421B and the one humidity sensor 422 are disposed in the sensor chamber Rs. In an example illustrated in FIG. 14, description is given of a case where the two pressure sensors 421A and 421B and the one humidity sensor 422 are provided. However, as is the case with FIG. 8C or FIG. 8D, only one pressure sensor 421 and one humidity sensor 422 may be provided.

In the circuit substrate 400, the second sub-passage 306 is disposed on a rear surface side of the substrate main body 401. Accordingly, it is possible to cool down the entirety of the substrate main body 401 by using the gas to be measured 30 that passes through the second sub-passage 306.

4.2 Structure of Temperature Detection Unit 451

A temperature detection unit 451 is provided at an edge on an upstream side of the base portion 402 and a corner of the base portion 402 on a protrusion 403 side. The temperature detection unit 451 constitutes one of detection units which detect the physical quantity of the gas to be measured 30 that flows through the main passage 124, and is provided in the circuit substrate 400. The circuit substrate 400 includes a protrusion 450 that protrudes from the second sub-passage inlet 306a of the second sub-passage 306 toward an upstream side of the gas to be measured 30, and the temperature detection unit 451 includes a chip-type temperature sensor 453 that is provided at the protrusion 450 on the rear surface of the circuit substrate 400. The temperature sensor 453 and a wiring portion thereof are covered with a synthetic resin material to prevent occurrence of electrolytic corrosion due to adherence of salt water.

For example, as illustrated in FIG. 8A, the upstream side outer wall 336 of the measurement section 331, which constitutes the housing 302, is recessed toward a downstream side at the central portion of the measurement section 331 at which the second sub-passage inlet 306a is provided, and the protrusion 450 of the circuit substrate 400 protrudes from the recessed upstream side outer wall 336 toward an upstream side. A front end of the protrusion 450 is disposed at a position that is further recessed in comparison to a surface on the most upstream side of the upstream side outer wall 336. The temperature detection unit 451 is provided at the protrusion 450 to face the rear surface of the circuit substrate 400, that is, the second sub-passage 306 side.

The second sub-passage inlet 306a is formed downstream of the temperature detection unit 451. Accordingly, the gas to be measured 30, which flows into the second sub-passage 306 from the second sub-passage inlet 306a, comes into contact with the temperature detection unit 451, and flows into the second sub-passage inlet 306a. When the gas to be measured 30 comes into contact with the temperature detection unit 451, a temperature is detected. The gas to be measured 30, which comes into contact with the temperature detection unit 451, flows into the second sub-passage 306 from the second sub-passage inlet 306a, passes through the second sub-passage 306, and is discharged from the second sub-passage outlet 306b to the main passage 124.

4.3 Fixing of Circuit Substrate 400 through Resin Molding Process, and Effect Thereof An oblique line portion in FIG. 12 and FIG. 14 indicates the fixing surface 432 and the fixing surface 434 for covering the circuit substrate 400 with a thermoplastic resin that is used in the resin molding process so as to fix the circuit substrate 400 to the housing 302 in the resin molding process. It is important to maintain high accuracy so that a relationship between shapes of the measurement flow path surface 430 and the flow rate detection unit 602 provided in the measurement flow path surface 430, and the sub-passage becomes a defined relationship.

In the resin molding process, the sub-passage is molded, and the circuit substrate 400 is simultaneously fixed to the housing 302 that molds the sub-passage, and thus it is possible to maintain a relationship between the sub-passage, and the measurement flow path surface 430 and the flow rate detection unit 602 with very high accuracy. That is, the circuit substrate 400 is fixed to the housing 302 in the resin molding process, it is possible to position and fix the circuit substrate 400 in a mold for molding the housing 302 provided with the sub-passage with high accuracy. When a high-temperature thermoplastic resin is injected into the mold, the sub-passage is molded with high accuracy, and the circuit substrate 400 is fixed with high accuracy. Accordingly, it is possible to suppress an error or a deviation, which occurs for each circuit substrate 400, to a very small value. As a result, it is possible to greatly improve the measurement accuracy of the circuit substrate 400.

In this example, the outer periphery of the base portion 402 of the substrate main body 401 is covered with the fixing portions 372 and 373 of the molding resin that molds the housing 302, and is set to the fixing surfaces 432 and 434.

5. Circuit Configuration of Physical-Quantity Detection Device 300

5.1 Signal Processing of Physical-Quantity Detection Device 300

Figure 16:
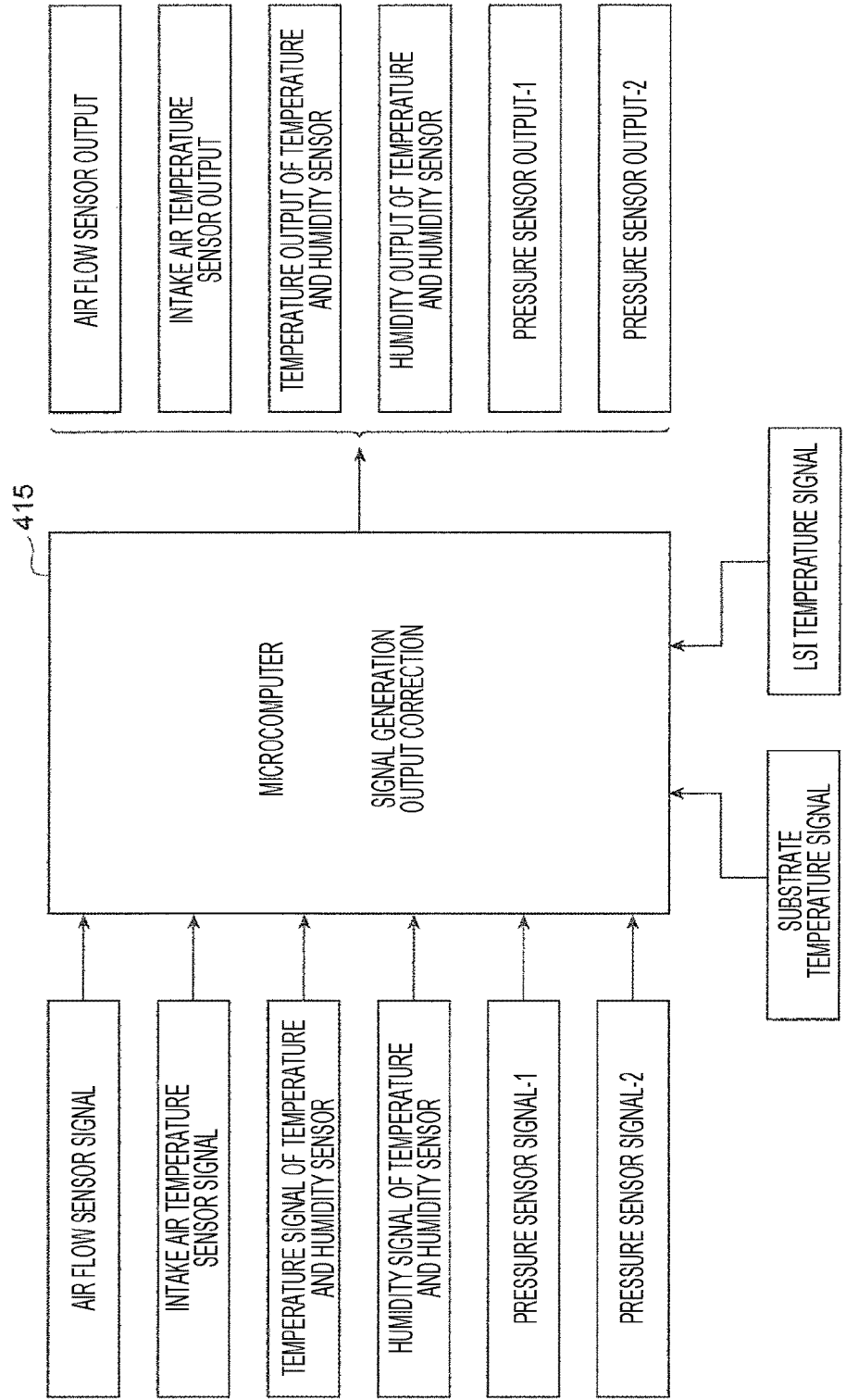
FIG. 16 is a block diagram illustrating an input and an output of the physical-quantity detection device.

FIG. 16 illustrates an input-output relationship of a signal of the physical-quantity detection device 300. In this example, the physical-quantity detection sensor is mounted on both of the front surface and the rear surface of one sheet of the circuit substrate 400 to realize miniaturization of the substrate. Accordingly, even in the signal processing, all signals from the physical-quantity sensors are fetched with one microcomputer 415 so as to reduce the number of electronic circuit components, and generation and correction of a signal that is readable in the control device 200 are made. In addition, as illustrated in FIG. 7 and FIG. 9, the circuit substrate 400 transmits the electrical signals to the control device 200 through an AL wire 324 and an external terminal 323.

5.2 Entirety of Circuit Configuration of Physical-Quantity Detection Device 300

Figure 17:
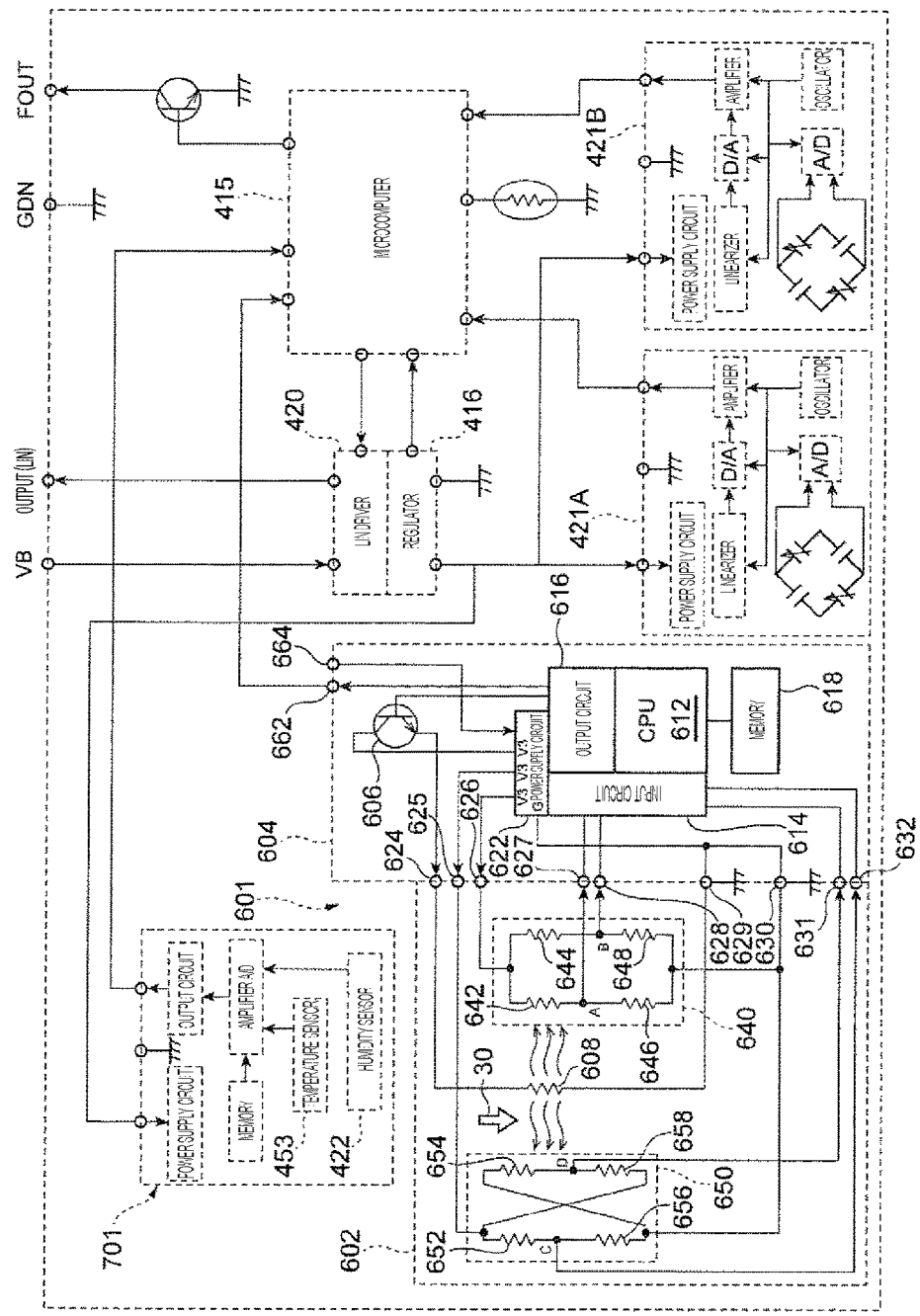
FIG. 17 is a view illustrating one example of a circuit configuration of the physical-quantity detection device.

FIG. 17 is a circuit diagram of the physical-quantity detection device 300. The physical-quantity detection device 300 includes a flow rate detection circuit 601, and a temperature and humidity detection circuit 701.

The flow rate detection circuit 601 includes the flow rate detection unit 602 having a heat generation body 608 and a processing unit 604. The processing unit 604 controls the amount of heat generation of the heat generation body 608 in the flow rate detection unit 602, and outputs a signal indicating the flow rate to the microcomputer 415 through a terminal 662 on the basis of an output of the flow rate detection unit 602. To perform the processing, the processing unit 604 includes a central processing unit (hereinafter, referred to as "CPU") 612, an input circuit 614, an output circuit 616, a memory 618 that stores data indicating a relationship between a correction value or a measurement value and the flow rate, and a power supply circuit 622 that supplies a constant voltage to circuits in which the voltage is necessary. DC power is supplied to the power supply circuit 622 from an external power supply such as an in-vehicle battery through a terminal 664 and a ground terminal (not illustrated).

The heat generation body 608, which heats the gas to be measured 30, is provided in the flow rate detection unit 602. A voltage V1 is supplied from the power supply circuit 622 to a collector of a transistor 606 that constitutes a current supply circuit of the heat generation body 608, a control signal is applied to a base of the transistor 606 from the CPU 612 through the output circuit 616, and a current is supplied from the transistor 606 to the heat generation body 608 through a terminal 624 on the basis of the control signal. The amount of current supplied to the heat generation body 608 is controlled by the control signal that is applied to the transistor 606, which constitutes a current supply circuit of the heat generation body 608, from the CPU 612 through the output circuit 616. The processing unit 604 controls the amount of heat generation of the heat generation body 608 so that the gas to be measured 30 is heated with the heat generation body 608 and a temperature of the gas to be measured 30 becomes higher than a current temperature by a predetermined temperature, for example, 100° C.

The flow rate detection unit 602 includes a heat generation control bridge 640 that controls the amount of heat generation of the heat generation body 608, and a flow rate detection bridge 650 that measures a flow rate. A constant voltage V3 is supplied to one end of the heat generation control bridge 640 from the power supply circuit 622 through a terminal 626, and the other end of the heat generation control bridge 640 is connected to a ground terminal 630. In addition, a constant voltage V2 is supplied to one end of the flow rate detection bridge 650 from the power supply circuit 622 through a terminal 625, and the other end of the flow rate detection bridge 650 is connected to the ground terminal 630.

The heat generation control bridge 640 includes a resistor 642 that is a temperature measuring resistor of which a resistance value varies based on a temperature of the gas to be measured 30 that is heated, and the resistor 642, a resistor 644, a resistor 646, and a resistor 648 constitute a bridge circuit. A potential difference between an intersection A of the resistor 642 and the resistor 646, and an intersection B of the resistor 644 and the resistor 648 is input to the input circuit 614 through a terminal 627 and a terminal 628, and the CPU 612 controls the amount of heat generation of the heat generation body 608 by controlling a current that is supplied from the transistor 606 so that the potential difference between the intersection A and the intersection B becomes a predetermined value, in this embodiment, a zero bolt. The flow rate detection circuit 601 illustrated in FIG. 17 heats the gas to be measured 30 with the heat generation body 608 so that a temperature of the gas to be measured 30 becomes higher than an original temperature of the gas to be measured 30 by a constant temperature, for example, typically 100° C. Resistance values of the respective resistors, which constitute the heat generation control bridge 640, are set so that a potential difference between the intersection A and the intersection B becomes a zero bolt when the temperature of the gas to be measured 30 heated with the heat generation body 608 becomes higher than the original temperature thereof by a constant temperature, for example, typically 100° C. so as to perform heating control with high accuracy. Accordingly, in the flow rate detection circuit 601, the CPU 612 controls a current supplied to the heat generation body 608 so that the potential difference between the intersection A and the intersection B becomes a zero bolt.

The flow rate detection bridge 650 is constituted by four temperature measuring resistors including a resistor 652, a resistor 654, a resistor 656, and a resistor 658. The four temperature measuring resistors are disposed along the flow of the gas to be measured 30, the resistor 652 and the resistor 654 are disposed on an upstream side in the flow path of the gas to be measured 30 in comparison to the heat generation body 608, and the resistor 656 and the resistor 658 are disposed on a downstream side in the flow path of the gas to be measured 30 in comparison to the heat generation body 608. The resistor 652 and the resistor 654 are disposed at the same distance from the heat generation body 608, and the resistor 656 and the resistor 658 are disposed at the same distance from the heat generation body 608 so as to improve measurement accuracy.

A potential difference between an intersection C of the resistor 652 and the resistor 656, and an intersection D of the resistor 654 and the resistor 658 is input to the input circuit 614 through a terminal 632 and a terminal 631. The respective resistors of the flow rate detection bridge 650 are set so that a potential difference between the intersection C and the intersection D becomes zero, for example, in a state in which the flow of the gas to be measured 30 is zero so as to improve measurement accuracy. Accordingly, for example, in a state in which the potential difference between the intersection C and the intersection D is a zero bolt, the CPU 612 outputs an electrical signal, which indicates that the flow rate in the main passage 124 is zero, from the terminal 662 on the basis of a measurement result indicating that the flow rate of the gas to be measured 30 is zero.

In a case where the gas to be measured 30 flows in an arrow direction in FIG. 17, the resistor 652 and the resistor 654, which are disposed on an upstream side, are cooled down by the gas to be measured 30, and the resistor 656 and the resistor 658, which are disposed on a downstream side of the gas to be measured 30, are heated by the gas to be measured 30 that is heated by the heat generation body 608, and thus the temperature of the resistor 656 and the resistor 658 rises. Accordingly, a potential difference occurs between the intersection C and the intersection D of the flow rate detection bridge 650, and the potential difference is input to the input circuit 614 through the terminal 631 and the terminal 632. The CPU 612 searches data, which is stored in the memory 618 and indicates a relationship between the potential difference and the flow rate in the main passage 124, on the basis of the potential difference between the intersection C and the intersection D of the flow rate detection bridge 650 to obtain the flow rate in the main passage 124. The electrical signal, which is obtained in this manner and indicates the flow rate in the main passage 124, is output through the terminal 662. Furthermore, new reference numerals are given to the terminal 664 and the terminal 662 illustrated in FIG. 17, but the terminals are included in the connection terminal 412 illustrated in FIG. 12.

The memory 618 stores data that indicates a relationship between the potential difference between the intersection C and the intersection D, and the flow rate in the main passage 124. In addition, the memory 618 stores correction data that is obtained on the basis of an actually measured value of a gas after production of the circuit substrate 400 and is configured to reduce a measurement error such as a deviation.

The temperature and humidity detection circuit 701 includes an input circuit such as amplifier and A/D which input a detection signal from the temperature sensor 453 and the humidity sensor 422, an output circuit, a memory that stores data indicating a relationship between a correction value or a temperature and absolute humidity, and a power supply circuit that supplies a constant voltage to a circuit in which the voltage is necessary. Signals, which are output from the flow rate detection circuit 601 and the temperature and humidity detection circuit 701, are input to the microcomputer 415. The microcomputer 415 includes a flow rate calculation unit, a temperature calculation unit, and an absolute humidity calculation unit, calculates the flow rate, the temperature, and the absolute humidity, which are physical quantities of the gas to be measured 30, on the basis of the signals, and outputs the resultant calculated values to the control device 200.

Connection between the physical-quantity detection device 300 and the control device 200 is established with a communication cable, and a communication using a digital signal is performed therebetween in accordance with a communication standard such as SENT, LIN, and CAN. In this example, a signal is input from the microcomputer 415 to an LIN driver 420, and an LIN communication is performed from the LIN driver 420. Information, which is output from the LIN driver of the physical-quantity detection device 300 to the control device 200, is output in a superposition manner through a digital communication by using single or two communication cables.

The absolute humidity calculation unit of the microcomputer 415 calculates absolute humidity on the basis of relative humidity information and temperature information which are output from the humidity sensor 422, and performs a process of correcting the absolute humidity on the basis of an error. The absolute humidity after correction, which is calculated by the absolute humidity calculation unit, is used for various engine operation controls in the control device 200. In addition, the control device 200 may directly use information of an overall error for various engine operation controls.

Hereinbefore, embodiments of the invention have been described in detail, but the invention is not limited to the embodiments, and various design changes can be made in a range not departing from the spirit of the invention described in claims. For example, the embodiments have been described in detail for easy explanation of the invention, but it is not limited to include all of the above-described configurations. In addition, a part of configurations of one embodiment can be substituted with configurations of another embodiment, and configurations of another embodiment may be added to configurations of one embodiment. In addition, addition, deletion, substitution of other configurations can be made to parts of configurations of respective embodiments.

REFERENCE SIGNS LIST 30 gas to be measured
124 main passage
300 physical-quantity detection device
302 housing
400 circuit substrate
404, 405, 406 through-hole
407, 408 cut-out portion
421A, 421B pressure sensor (third detection unit)
422 humidity sensor (second detection unit)
602 flow rate detection unit (first detection unit)

The invention claimed is:

1. A physical-quantity detection device that measures a physical quantity of a gas to be measured which passes through a main passage, comprising:
   a housing including a sub-passage into which the gas to be measured is taken from the main passage;
   at least one pressure sensor that is disposed in the sub-passage and detects a pressure of the gas to be measured;
   a humidity sensor that is disposed in the sub-passage and detects humidity of the gas to be measured; and
   a circuit substrate in which the pressure sensor and the humidity sensor are provided, and a detection signal of the humidity sensor and a detection signal of the pressure sensor are subjected to operation processing,
   wherein the pressure sensor and the humidity sensor are disposed in parallel in the sub-passage along a flow direction of the gas to be measured, and
   at least one of the pressure sensor is disposed on an upstream side in the flow direction of the gas to be measured, and the humidity sensor is disposed on a downstream side in the flow direction of the gas to be measured in comparison to the at least one of the pressure sensor.

2. The physical-quantity detection device according to claim 1,
   wherein the pressure sensor and the humidity sensor are disposed at positions which are offset with respect to the flow direction of the gas to be measured in the sub-passage.

3. The physical-quantity detection device according to claim 2,
   wherein the pressure sensor has a shape in which a projection area in the flow direction of the gas to be measured is greater in comparison to the humidity sensor, and the pressure sensor and the humidity sensor are disposed in such a manner that the projection area of the humidity sensor enters a range of the projection area of the pressure sensor.

4. The physical-quantity detection device according to claims 1,
   wherein the pressure sensor includes a first pressure sensor and a second pressure sensor which are respectively disposed on an upstream side and a downstream side in the flow direction of the gas to be measured with the humidity sensor interposed between the first pressure sensor and the second pressure sensor.

5. The physical-quantity detection device according to claim 1,
   wherein the humidity sensor detects both humidity and a temperature of the gas to be measured.

* * * * *